United States Patent
Wakita et al.

(10) Patent No.: US 12,171,586 B2
(45) Date of Patent: Dec. 24, 2024

(54) OUTPUT CONTROL DEVICE, OUTPUT CONTROL METHOD, AND PROGRAM

(71) Applicant: SONY CORPORATION, Tokyo (JP)

(72) Inventors: Yoshihiro Wakita, Tokyo (JP); Naoya Sazuka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 325 days.

(21) Appl. No.: 16/335,047

(22) PCT Filed: Oct. 5, 2017

(86) PCT No.: PCT/JP2017/036345
§ 371 (c)(1),
(2) Date: Mar. 20, 2019

(87) PCT Pub. No.: WO2018/100879
PCT Pub. Date: Jun. 7, 2018

(65) Prior Publication Data
US 2019/0274630 A1  Sep. 12, 2019

(30) Foreign Application Priority Data

Nov. 30, 2016 (JP) ................. 2016-232514
Nov. 30, 2016 (JP) ................. 2016-232659

(51) Int. Cl.
*A61B 5/00* (2006.01)
*A61B 5/16* (2006.01)
(Continued)

(52) U.S. Cl.
CPC .............. *A61B 5/7275* (2013.01); *A61B 5/00* (2013.01); *A61B 5/165* (2013.01); *A61B 5/4064* (2013.01);
(Continued)

(58) Field of Classification Search
CPC ....... A61B 5/7264; A61B 5/00; A61B 5/4064; A61B 5/681; A61B 5/7228; A61B 5/7275;
(Continued)

(56) References Cited

U.S. PATENT DOCUMENTS 6,527,700 B1   3/2003  Manico et al.
2008/0001735 A1*  1/2008  Tran ..................... A61B 5/0488
                                                340/539.22
(Continued)

FOREIGN PATENT DOCUMENTS

CN    105807913 A    7/2016
JP    H05-084222 A   4/1993
(Continued)

OTHER PUBLICATIONS

Neuman, M. R. "Biopotential Electrodes." The Biomedical Engineering Handbook: Second Ed. Joseph D. Bronzino; Boca Raton: CRC Press LLC, 2000 (Year: 2000).*

*Primary Examiner* — Pamela M. Bays
(74) *Attorney, Agent, or Firm* — Paratus Law Group, PLLC

(57) ABSTRACT

There is provided an output control device, an output control method, and a program to provide technologies for enabling users to control their internal states more easily. The output control device including: an output control unit configured to control output of output information in accordance with a change in a state point in a physiological index space corresponding to a physiological index value based on biosensors. The output control unit controls the output of the output information in accordance with distribution density of previous state points for which a current state point serves as a standard in the physiological index space.

20 Claims, 20 Drawing Sheets

(51) Int. Cl.
*A61M 21/02* (2006.01)
*G16H 50/20* (2018.01)

(52) U.S. Cl.
CPC .......... *A61B 5/7228* (2013.01); *A61B 5/7264* (2013.01); *A61M 21/02* (2013.01); *A61B 5/486* (2013.01); *A61B 5/681* (2013.01); *G16H 50/20* (2018.01)

(58) Field of Classification Search
CPC ....... A61B 5/486; A61B 5/4836; A61B 5/165; A61M 21/02
See application file for complete search history.

(56) References Cited

U.S. PATENT DOCUMENTS

| | | | |
|---|---|---|---|
| 2011/0001636 A1* | 1/2011 | Hedrick | G01D 7/002 340/945 |
| 2011/0029248 A1* | 2/2011 | Saeed | A61B 5/7275 702/19 |
| 2011/0119212 A1* | 5/2011 | De Bruin | A61B 5/0476 706/12 |
| 2014/0149325 A1* | 5/2014 | Clifton | A61B 5/0205 706/12 |

FOREIGN PATENT DOCUMENTS

| | | |
|---|---|---|
| JP | H10-076012 A | 3/1998 |
| JP | 2004-222818 A | 8/2004 |
| JP | 2007-529283 A | 10/2007 |
| JP | 2009-082299 A | 4/2009 |
| JP | 2012-161558 A | 8/2012 |
| JP | 2013-027570 A | 2/2013 |

\* cited by examiner

FIG. 2
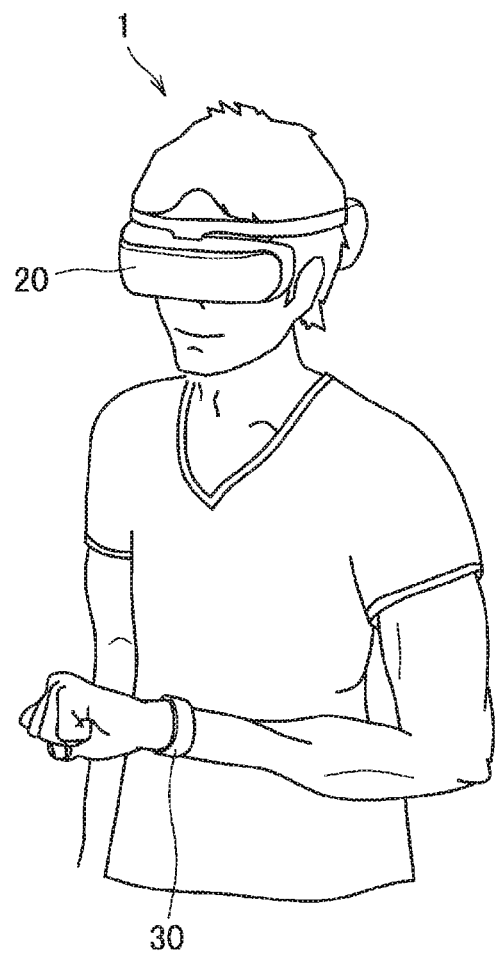
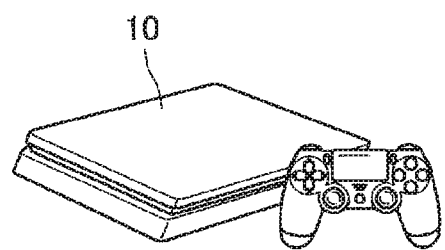

FIG. 6

| MODAL | PHYSIOLOGICAL INDEX | PHYSIOLOGICAL MEANING |
|---|---|---|
| PERIPHERAL BLOODSTREAM (BLOODSTREAM AROUND SKIN) | CHANGE IN BLOOD FLOW VOLUME | CONTRACTION OF ARTERIOLE: SYMPATHETIC ACTIVITY REACTION CHANGE IN CARDIAC OUTPUT: SYMPATHETIC ACTIVITY REACTION (HOWEVER, CHANGE IN CARDIAC OUTPUT IS ALSO MADE BY EXERCISE) |
| | RATIO OF ARTERIOLE TO CAPILLARY | CONTRACTION OF ARTERIOLE: SYMPATHETIC ACTIVITY REACTION |
| | RATIO OF FACE TO HAND | PATTERN OF CONTRACTION OF ARTERIOLE: SYMPATHETIC ACTIVITY REACTION AND PARASYMPATHETIC ACTIVITY REACTION |
| HEARTBEAT (PULSE) | HEART RATE | ADJUSTMENT OF CARDIAC OUTPUT: SYMPATHETIC ACTIVITY REACTION (HOWEVER, ADJUSTMENT OF CARDIAC OUTPUT IS ALSO CHANGED BY EXERCISE) |
| | CARDIAC VARIABILITY | BLOOD PRESSURE-RELATED VARIABILITY: SYMPATHETIC ACTIVITY REACTION AND PARASYMPATHETIC ACTIVITY REACTION RESPIRATION-RELATED VARIABILITY: PARASYMPATHETIC ACTIVITY REACTION |
| PERSPIRATION | PALM PERSPIRATION (INCLUDING WRIST) | MENTAL PERSPIRATION: SYMPATHETIC ACTIVITY REACTION |
| BRAIN WAVE | FREQUENCY COMPONENT FOR EACH ELECTRODE | VARIOUS |

FIG. 10
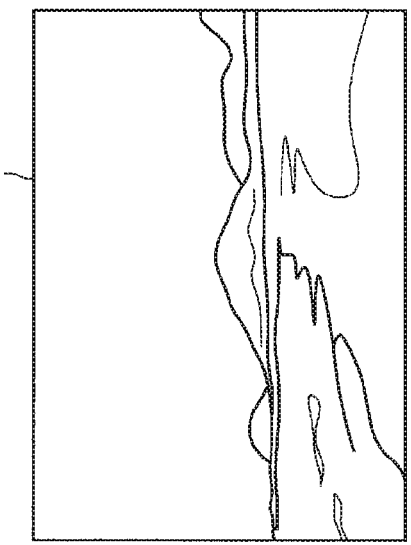
IM-2
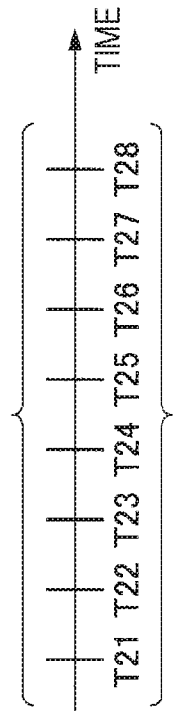
| LABEL | TIME | STATE POINT |
|---|---|---|
| RELAX | T21 | E21 |
| | T22 | E22 |
| | T23 | E23 |
| | T24 | E24 |
| | T25 | E25 |
| | T26 | E26 |
| | T27 | E27 |
| | T28 | E28 |
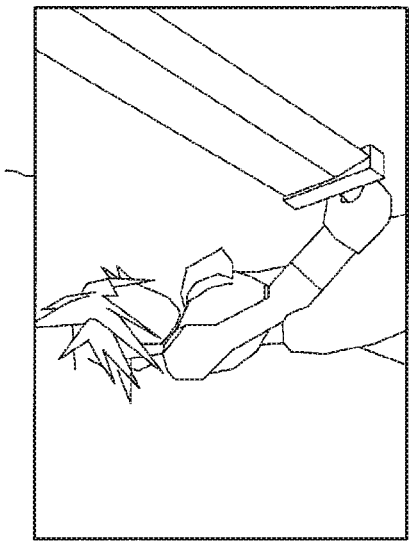
IM-1
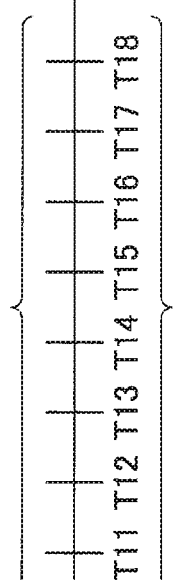
| LABEL | TIME | STATE POINT |
|---|---|---|
| CONCENT-RATION | T11 | E11 |
| | T12 | E12 |
| | T13 | E13 |
| | T14 | E14 |
| | T15 | E15 |
| | T16 | E16 |
| | T17 | E17 |
| | T18 | E18 |

OUTPUT CONTROL DEVICE, OUTPUT CONTROL METHOD, AND PROGRAM

CROSS REFERENCE TO PRIOR APPLICATION

This application is a National Stage Patent Application of PCT International Patent Application No. PCT/JP2017/036345 (filed on Oct. 5, 2017) under 35 U.S.C. § 371, which claims priority to Japanese Patent Application Nos. 2016-232514 (filed on Nov. 30, 2016) and 2016-232659 (filed on Nov. 30, 2016), which are all hereby incorporated by reference in their entirety.

TECHNICAL FIELD

The present disclosure relates to an output control device, an output control method, and a program.

BACKGROUND ART

In recent years, maintaining normal autonomic nerve activity has been seen as more important. For example, a technology for diagnosing normality of autonomic nerve activity has been disclosed (for example, see Patent Literature 1). In addition, autonomic nerve activity is known to be involved in internal states of users (for example, a concentration state, a tension state, a relaxed state, and the like).

CITATION LIST

Patent Literature

Patent Literature 1: JP H5-84222A

DISCLOSURE OF INVENTION

Technical Problem

Here, it is important for users to be able to control their internal states to some extent in various occasions. Accordingly, it is preferable to provide technologies for enabling users to control their internal states more easily.

Solution to Problem

According to the present disclosure, there is provided an output control device including: an output control unit configured to control output of output information in accordance with a change in a state point in a physiological index space corresponding to a physiological index value based on a biosensor.

According to the present disclosure, there is provided an output control method including: by a processor, controlling output of output information in accordance with a change in a state point in a physiological index space corresponding to a physiological index value based on a biosensor.

According to the present disclosure, there is provided a program causing a computer to function as an output control device including an output control unit configured to control output of output information in accordance with a change in a state point in a physiological index space corresponding to a physiological index value based on a biosensor.

Advantageous Effects of Invention

According to the present disclosure, as described above, it is possible to provide a technology for enabling a user to control his or her internal state more easily. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 2 is a diagram illustrating a configuration example of an information processing system according to an embodiment of the present disclosure.

FIG. 6 is a diagram illustrating examples of physiological index values detected by various sensors.

FIG. 10 is an explanatory diagram illustrating an example of association of labels with state points.

MODE(S) FOR CARRYING OUT THE INVENTION

Figure 1:
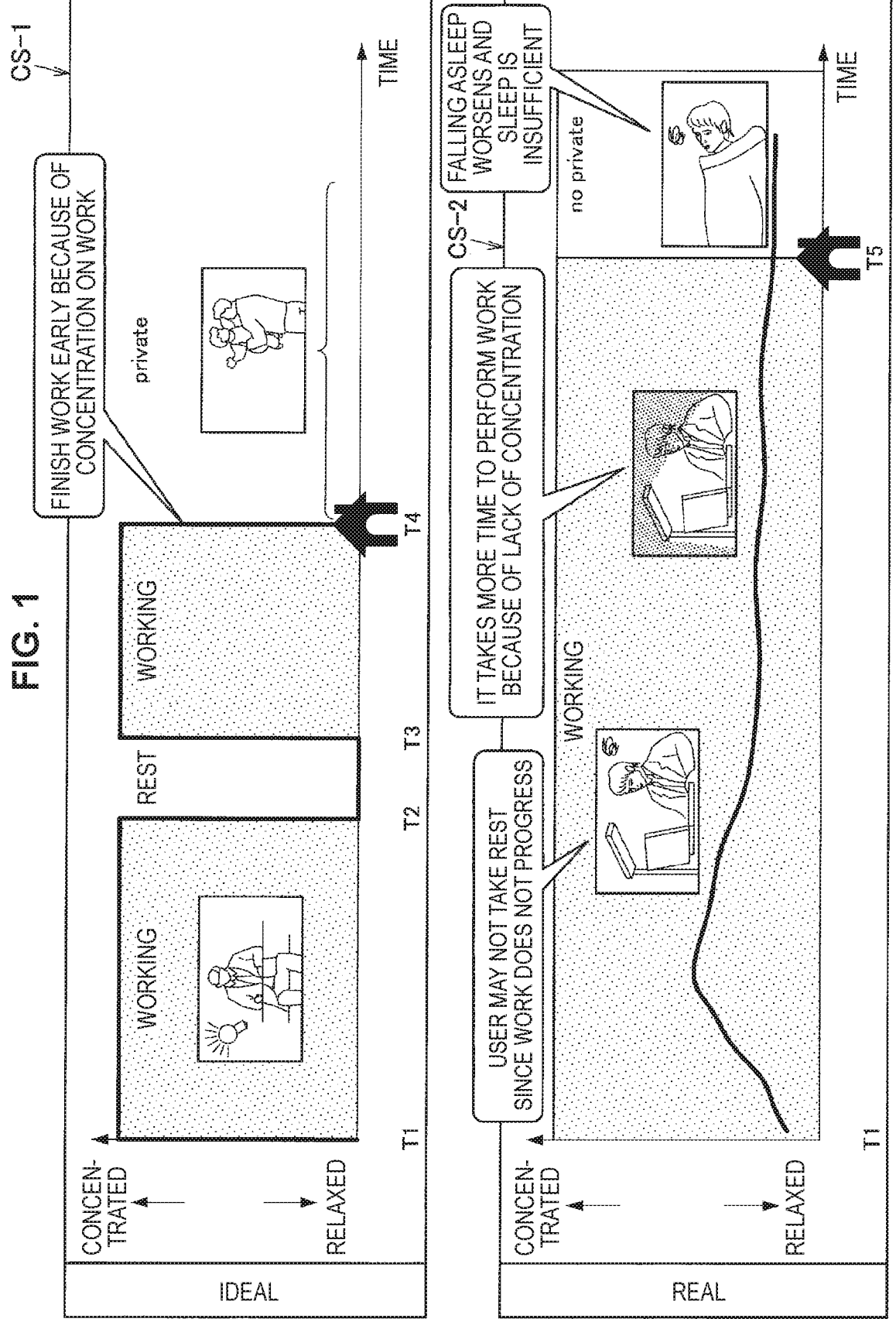
FIG. 1 is an explanatory diagram illustrating an example of the importance of control of an internal state.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that, in the present specification and the drawings, structural elements that have substantially the same or similar function and structure are sometimes distinguished from each other using different numbers after the same reference sign. However, when there is no need in particular to distinguish structural elements that have substantially the same or similar function and structure, the same reference sign alone is attached. Further, there are cases in which similar structural elements of different embodiments are distinguished by adding the same reference numeral followed by different letters. However, in a case where it is not necessary to particularly distinguish each of similar structural element, only the same reference signs are attached.

Note that the description will be made in the following order.

1. Overview of control of internal state
2. Embodiment of control of internal state
2.1. System configuration example
2.2. Functional configuration example of information processing device
2.3. Functional configuration example of display device
2.4. Functional configuration example of output control device
2.5. Function details of control of internal state
2.5.1. Various physiological index values
2.5.2. Physiological index space
2.5.3. Feedback in accordance with change in state point
2.5.4. Mental stretch training
2.5.5. Mental stretch training using content appreciation
2.5.6. Unsupervised individualization learning
2.5.7. Supervised individualization learning
2.5.8. Mental switch training
3. Overview of generation of estimator
4. Embodiment of generation of estimator
5. Hardware configuration example
6. Conclusion

1. OVERVIEW OF CONTROL OF INTERNAL STATE

In recent years, maintaining normal autonomic nerve activity has been seen as more important. For example, a technology for diagnosing normality of autonomic nerve activity has been disclosed. In addition, autonomic nerve activity is known to be involved in internal states of users (for example, a concentration state, a tension state, a relaxation state, and the like). Here, it is important for users to be able to control their internal states to some extent in various occasions. First, the importance of control of one's internal state will be described giving a specific example.

FIG. 1 is an explanatory diagram illustrating an example of the importance of control of an internal state. Referring to FIG. 1, a pattern (ideal pattern CS-1) considered to be ideal is illustrated as a pattern of a daily life of a user. In addition, a pattern (real pattern CS-2) that actually occurs is illustrated as a pattern of a daily life of the user.

In the ideal pattern CS-1, the user maintains his or her internal state as a concentrated state during working time (time T1 to time T2). In addition, the user switches his or her internal state from the concentrated state to the relaxed state promptly for rest time and maintains the internal state as the relaxed state (time T2 to time T3). Then, after the rest time finishes, the user switches his or her internal state from the relaxed state to the concentrated state promptly and maintains the concentrated state (time T3 to time T4).

In this way, in the ideal pattern CS-1, the user performs the switching of his or her internal state quickly and maintains the internal state. As a result, the user can finish his or her work quickly and have private time (after time T4).

On the other hand, in the real pattern CS-2, the user does not maintain his or her internal state as a concentrated state even during working time. As a result, since his or her work does not progress, the user has to continuously work even during rest time and does not switch his or her internal state to the relaxed state. Then, since the user does not switch his or her internal state and take appropriate rest, the concentrated state gradually worsens, and thus it takes more time to perform the work.

In this way, in the real pattern CS-2, the user does not be able to switch his or her internal state promptly and maintain a preferred internal state. As a result, since the user does not be able to finish his or her work promptly and may not have private time, the user may not fall asleep and thus a lack of sleep occurs (after time T5). Since the user lacks sleep, the user does not switch his or her internal state promptly even on the following day and will not be able to maintain the internal state.

As understood from the example illustrated in FIG. 1, it is important for users to be able to control their internal states to some extent on various occasions. Biofeedback and neurofeedback are known as technologies for enabling users to control their internal states. However, biofeedback and neurofeedback are not sufficient as technologies for enabling users to control their internal states.

As one method of biofeedback and neurofeedback, there is a technology for performing feedback in which a more preferable result is given when a certain parameter is higher. In the technology, when feedback is performed so that the degree of parasympathetic nerve activity increases, it is considered possible to allow users to relax. For example, the technology is considered to be effective for patients who are in an over-tension state or the like. In addition, in the technology, when feedback is performed so that the degree of sympathetic nerve activity increases in an internal state in which a user is not relatively relaxed and in high concentration, the degree of sympathetic nerve activity increases, and thus it is considered to be able to allow the user to concentrate.

However, when sympathetic nerves are excited to some extent or more, side effects are known to occur. For example, it is known that a user whose sympathetic nerves are excited to some extent or more may not be able to make a cool-headed determination in some cases. In addition, it is known that a user whose sympathetic nerves are excited to some extent or more shakes his or her hands in some cases. Accordingly, it is not considered appropriate to perform feedback simply for the purpose of increasing the degree of sympathetic nerve activity.

In addition, in the technology, feedback for the purpose of causing an internal state to reach a specific internal state has been attempted. Here, to prevent an influence of the feedback from being too strong, it is sufficient if the degree of convergence on optimum physiological index values is fed back. However, an optimum internal state generally differs from person to person. In addition, the optimum internal state can change in accordance with personal development. Therefore, it is difficult to ascertain an individual optimum internal state at a certain point in time without carrying out machine learning or the like for a long time.

Further, since a change in an internal state can be said to occur to cause a user to adapt to a change in an environment, the change in the internal state can be said to be meaningful. Accordingly, it is considered difficult to define which internal state is a preferable internal state of a user. It is not preferable to perform feedback for the purpose of an internal state of a user approaching an internal state defined in advance. In the present specification, in consideration of the foregoing circumstances, a technology for enabling a user to control his or her internal state more easily will be mainly described.

The overview of the control of the internal state has been described above.

2. EMBODIMENT OF CONTROL OF INTERNAL STATE

[2.1. System Configuration Example]

Next, a configuration example of an information processing system according to an embodiment of the present disclosure will be described with reference to the drawings. FIG. 2 is a diagram illustrating a configuration example of the information processing system according to an embodiment of the present disclosure. As illustrated in FIG. 2, the information processing system 1 includes an information processing device 10, a display device 20, and an output control device 30. The information processing device 10 and the display device 20 can be connected in a wired or wireless manner. In addition, the information processing device 10 and the output control device 30 can be connected in a wired or wireless manner.

The information processing device 10 generates an estimator that estimates an internal state of a user. For example, the information processing device 10 can generate the estimator by machine learning. Various kinds of data to be used in the machine learning may be received from the display device 20 or may be received from the output control device 30. In addition, the information processing device 10 estimates an internal state using the generated estimator and transmits the internal state to the output control device 30.

In addition, the information processing device 10 can reproduce content. Here, a kind of content is not particularly limited and may be video content or game content. Display of the content may be changed in accordance with a user manipulation. In addition, the content may include virtual reality (VR) content configured using VR. Note that, in the present specification, a case in which the information processing device 10 is mainly a game device is assumed, but the information processing device 10 is not limited to the game device. For example, the information processing device 10 may be a smartphone or may be a personal computer (PC).

The display device 20 outputs content reproduced by the information processing device 10. An internal state of the user viewing the content output by the display device 20 easily transitions to or is easily maintained at a certain internal state. In addition, in the present specification, a case in which the display device 20 is a head-mounted display (HMD) worn on the head of the user and includes a sensor that detects a physiological index value reflecting central nerve activity is mainly assumed.

In the present specification, a case in which a sensor that detects a physiological index value reflecting central nerve activity (hereinafter also referred to as "central data") is provided in the display device 20 will be mainly described. However, the sensor that detects a physiological index value reflecting central nerve activity may be provided in a device other than the display device 20 (for example, a magnetic resonance imaging (MRI) device or the like). In this case, the display device 20 may not be an HMD and may be a stationary display, a smartphone, or the like.

The output control device 30 includes a sensor that detects a physiological index value reflecting autonomic nerve activity of the user. In the example illustrated in FIG. 2, the output control device 30 is worn on a wrist of the user, but a position at which the output control device 30 is worn may be appropriately changed depending on a kind of a physiological index value to be detected. In addition, the output control device 30 estimates an internal state of the user on the basis of a physiological index value reflecting autonomic nerve activity (hereinafter also referred to as "peripheral data") of the user and controls output in accordance with an estimation result. At this time, when wired connection between the output control device 30 and the information processing device 10 is disconnected, the user can freely move while wearing the output control device 30.

The configuration example of the information processing system 1 according to the embodiment of the present disclosure has been described above.

[2.2. Functional Configuration Example of Information Processing Device]

Figure 3:
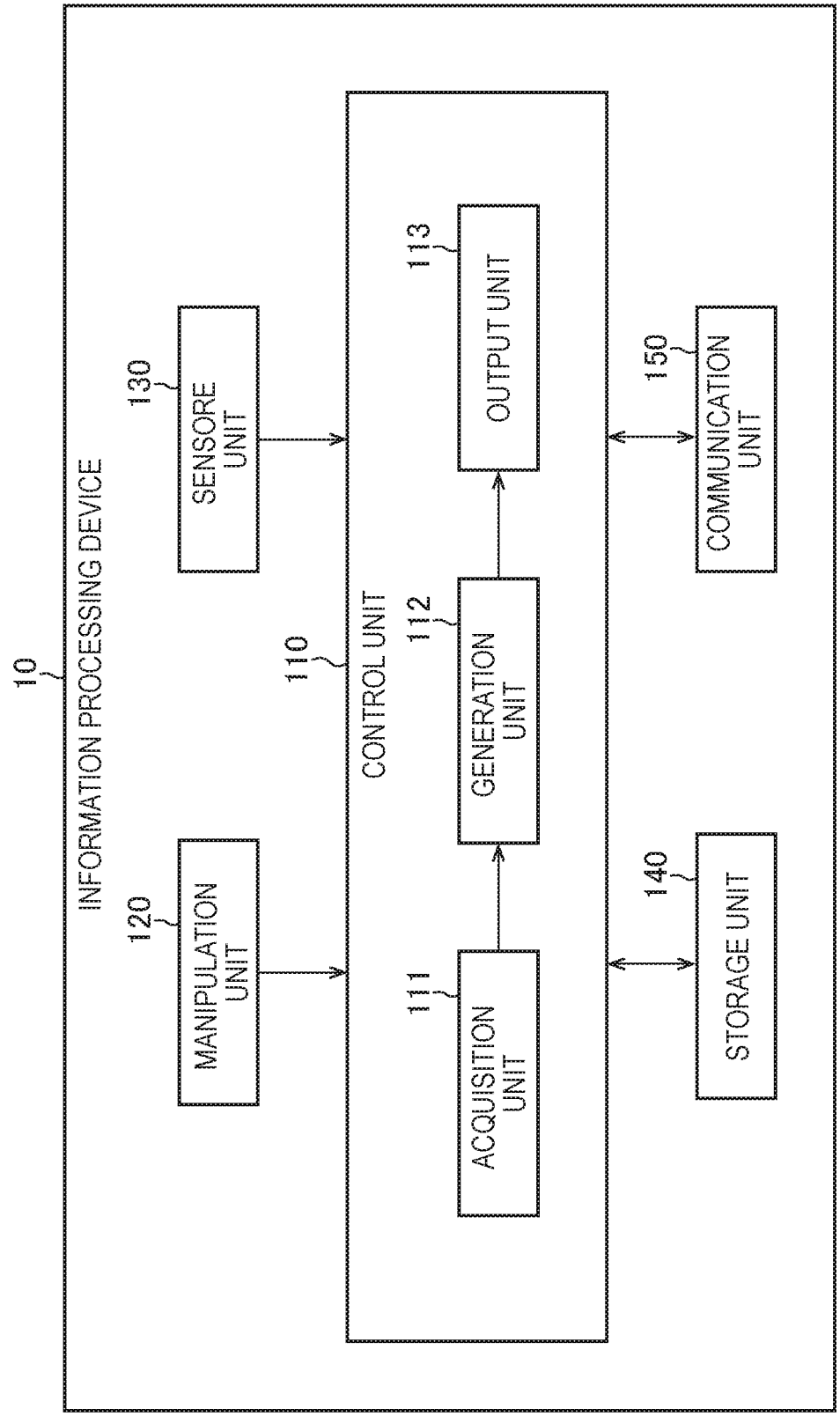
FIG. 3 is a block diagram illustrating a functional configuration example of the information processing device according to the embodiment.

Next, a functional configuration example of the information processing device 10 according to the embodiment of the present disclosure will be described. FIG. 3 is a block diagram illustrating a functional configuration example of the information processing device 10 according to the embodiment. As illustrated in FIG. 3, the information processing device 10 includes a control unit 110, a manipulation unit 120, a sensor unit 130, a storage unit 140, and a communication unit 150. Hereinafter, the functional blocks included in the information processing device 10 will be described.

The control unit 110 performs control of each unit of the information processing device 10. Note that the control unit 110 may be configured as, for example, a processing device including a single central processing unit (CPU), a plurality of CPUs or the like. In a case in which the control unit 110 is configured as a processing device including a CPU or the like, the processing device may be configured as an electronic circuit. As illustrated in FIG. 3, the control unit 110 includes an acquisition unit 111, a generation unit 112, and an output unit 113. The blocks included in the control unit 110 will be described in detail later.

The manipulation unit 120 includes an input device that receives various manipulations from the user. For example, the manipulation unit 120 may receive a manipulation input to content. At this time, display of the content may be changed on the basis of the manipulation input to the content. For example, in a case in which the information processing device 10 is a game device, the manipulation unit 120 may be a controller included in the game device.

The sensor unit 130 is a sensor that detects a position, an orientation, and a motion of the user (the display device 20). Here, the position, the orientation, and the motion of the user may be detected in any way. For example, the sensor unit 130 may include an image sensor and detect the position, the orientation, and the motion of the user on the basis of an image detected by the image sensor. The position, the orientation, and the motion of the user may be input to the content. At this time, display of the content may be changed on the basis of the position, the orientation, and the motion of the user input to the content.

The storage unit 140 includes a memory and is a recording device that stores a program to be executed by the control unit 110 or stores data necessary to execute the program. In addition, the storage unit 140 temporarily stores data for calculation by the control unit 110. Note that the storage unit 140 may be a magnetic storage device, may be a semiconductor storage device, may be an optical storage device, or may be a magneto-optical storage device.

The communication unit 150 includes a communication circuit and has a function of performing communication with another device. For example, the communication unit 150 includes a communication interface. For example, the communication unit 150 can perform communication with the display device 20 in a wired manner. Here, the communication unit 150 may perform communication with the display device 20 in a wireless manner. In addition, the communication unit 150 can perform communication with the output control device 30 in a wired manner. Here, the communication unit 150 may perform communication with the output control device 30 in a wireless manner.

The functional configuration example of the information processing device 10 according to the embodiment of the present disclosure has been described above.

[2.3. Functional Configuration Example of Display Device]

Figure 4:
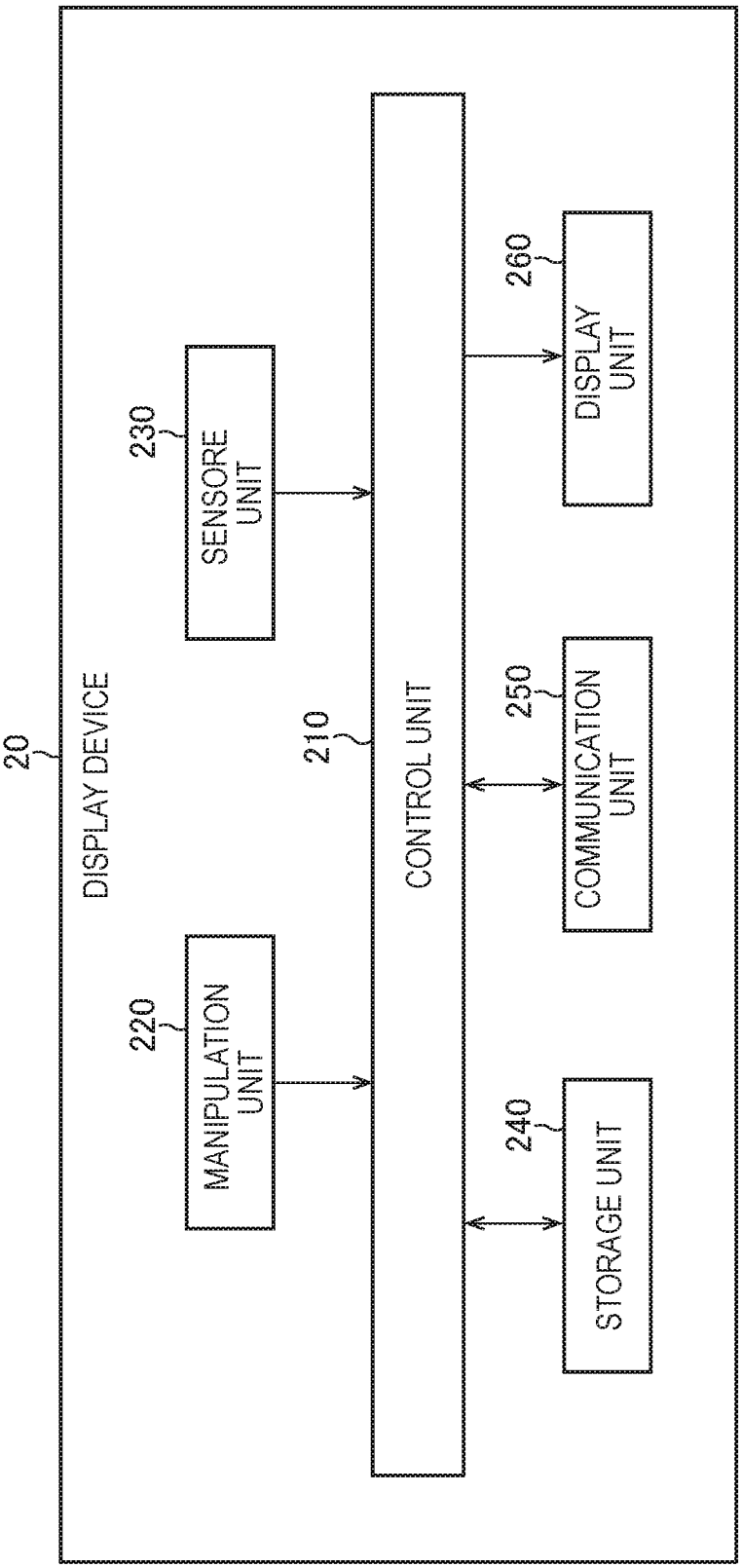
FIG. 4 is a block diagram illustrating a functional configuration example of a display device according to the embodiment.

Next, a functional configuration example of the display device 20 according to the embodiment of the present disclosure will be described. FIG. 4 is a block diagram illustrating a functional configuration example of the display device 20 according to the embodiment of the present disclosure. As illustrated in FIG. 4, the display device 20 includes a control unit 210, a manipulation unit 220, a sensor unit 230, a storage unit 240, a communication unit 250, and a display unit 260. Hereinafter, the functional blocks included in the display device 20 will be described.

The control unit 210 performs control of each unit of the display device 20. Note that the display device 20 may be configured as a processing device including a single central processing unit (CPU) or a plurality of CPUs or the like. In a case in which the control unit 210 is configured as a processing device including a CPU or the like, the processing device may be configured as an electronic circuit.

The manipulation unit 220 is an input device that receives a manipulation from the user. For example, the manipulation unit 220 may include a button for adjusting a position at which the display device 20 is worn on the user (for example, a button for moving the position of glasses of the HMD forward or backward, a button for adjusting the position of a band of the HMD forward or backward, or the like), a dial (for example, a dial for adjusting tightening of the band of the HMD or the like), and the like.

The sensor unit 230 includes a sensor that detects a physiological index value (central data) reflecting central nerve activity. In the present specification, a case in which central data includes brain waves will be mainly assumed. In this case, the sensor unit 230 may include a brain wave sensor. However, the central data is not particularly limited. For example, the central data may include magnetoencephalography (MEG). In this case, the sensor unit 230 may include a magnetoencephalographic sensor. Alternatively, the central data may include a measurement result by near-infrared spectroscopy (NIRS). In this case, the sensor unit 230 may include an NIRS sensor.

Note that, in the present specification, a case in which a position, an orientation, and a motion of the user is detected by the sensor 130 included in the information processing device 10 will be mainly assumed. However, the sensor unit 230 included in the display device 20 may include various sensors that detect a position, an orientation, and a motion of the user.

The storage unit 240 includes a memory and is a recording device that stores a program to be executed by the control unit 210 or stores data necessary to execute the program. In addition, the storage unit 240 temporarily stores data for calculation by the control unit 210. Note that the storage unit 240 may be a magnetic storage device, may be a semiconductor storage device, may be an optical storage device, or may be a magneto-optical storage device.

The communication unit 250 includes a communication circuit and has a function of performing communication with another device. For example, the communication unit 250 includes a communication interface. For example, the communication unit 250 can perform communication with the information processing device 10 in a wired manner. Here, the communication unit 250 may perform communication with the information processing device 10 in a wireless manner.

The display unit 260 outputs various kinds of information. For example, the display unit 260 may include a display capable of performing display which can be viewed by the user. The display may be a liquid crystal display or may be an organic electro-luminescence (EL) display.

The functional configuration example of the display device 20 according to the embodiment of the present disclosure has been described above.

[2.4. Functional Configuration Example of Output Control Device]

Figure 5:
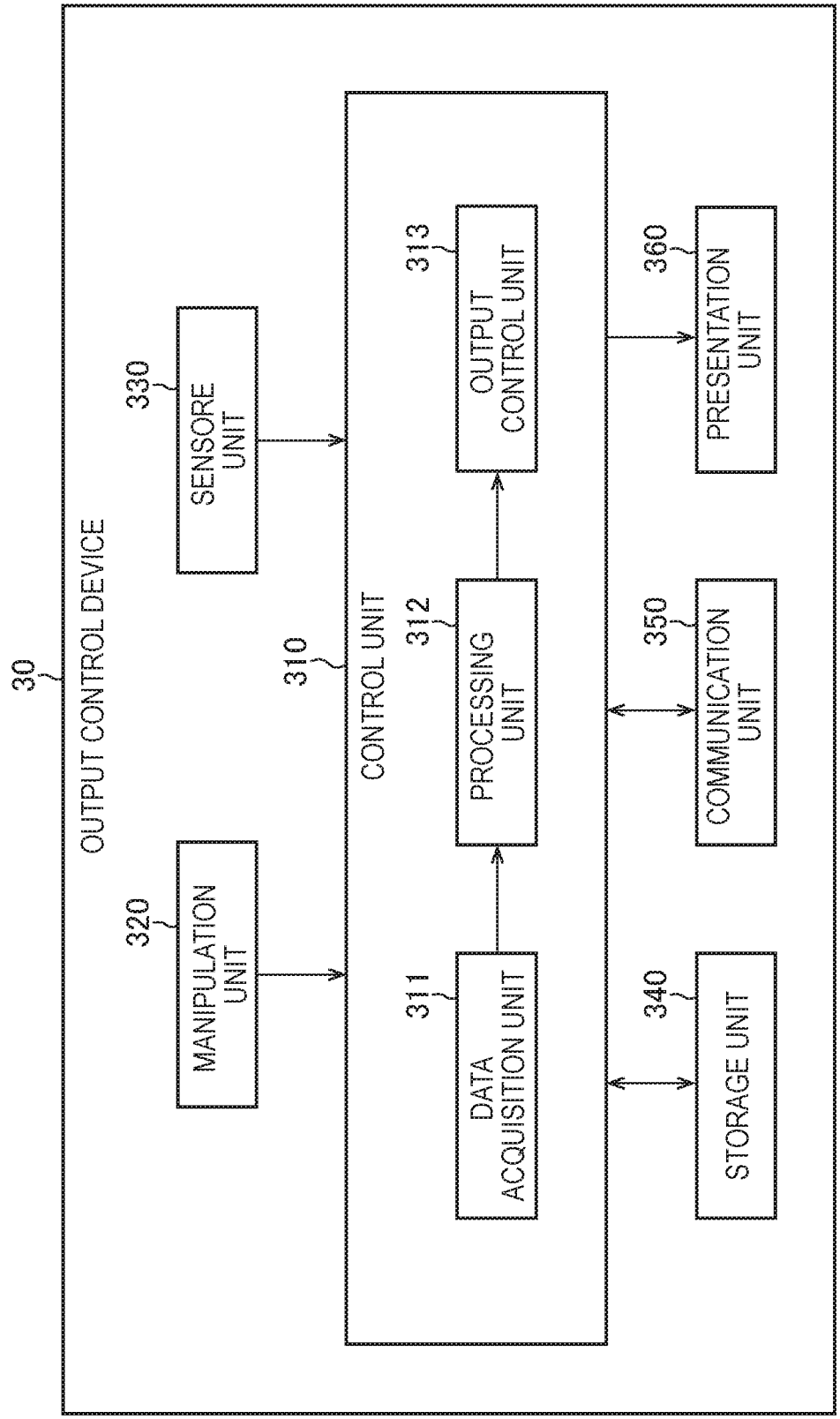
FIG. 5 is a block diagram illustrating a functional configuration example of an output control device according to the embodiment.

Next, a functional configuration example of the output control device 30 according to the embodiment of the present disclosure will be described. FIG. 5 is a block diagram illustrating a functional configuration example of the output control device 30 according to the embodiment. As illustrated in FIG. 5, the output control device 30 includes a control unit 310, a manipulation unit 320, a sensor unit 330, a storage unit 340, a communication unit 350, and a presentation unit 360. Hereinafter, the functional blocks included in the output control device 30 will be described.

The control unit 310 performs control of each unit of the output control device 30. Note that the control unit 310 may be configured as, for example, a processing device including a single central processing unit (CPU), a plurality of CPUs or the like. In a case in which the control unit 310 is configured as a processing device including a CPU or the like, the processing device may be configured as an electronic circuit.

The manipulation unit 320 includes an input device that receives various manipulations from the user. For example, when the manipulation unit 320 receives an input of a predetermined manipulation at a timing desired by the user, a flag is assigned to an internal state of the user at a point of time at which the predetermined manipulation is input. In this way, the internal state of the user to which the flag is assigned can be used for the user to control the internal state, as will be described below. Note that the term, the flag used in the present specification, is a broad concept also including a label used as a supervised signal in machine learning. Kinds of flags will be also described later.

The sensor unit 330 includes a sensor that detects a physiological index value reflecting autonomic nerve activity (peripheral data). For example, the peripheral data may include at least one of a peripheral bloodstream, a heartbeat, or perspiration. In this case, the sensor unit 330 may include at least one of a peripheral bloodstream sensor, an electrocardiographic sensor, a pulse sensor, or a perspiration sensor. Note that the pulse sensor and the peripheral bloodstream sensor may be separate sensors or may be the same sensor.

The storage unit 340 includes a memory and is a recording device that stores a program to be executed by the control unit 310 or stores data necessary to execute the program. In addition, the storage unit 340 temporarily stores data for calculation by the control unit 310. Note that the storage unit 340 may be a magnetic storage device, may be a semiconductor storage device, may be an optical storage device, or may be a magneto-optical storage device.

The communication unit 350 includes a communication circuit and has a function of performing communication with another device. For example, the communication unit 350 includes a communication interface. For example, the communication unit 350 can perform communication with the information processing device 10 in a wired manner. Here, the communication unit 350 may perform communication with the information processing device 10 in a wireless manner.

The presentation unit 360 outputs various kinds of information. For example, the presentation unit 360 may include a display capable of performing display which can be viewed by the user. The display may be a liquid crystal display or may be an organic electro-luminescence (EL) display. In addition, the presentation unit 360 may include a sound output device such as a speaker. Alternatively, the presentation unit 360 may include a tactile presentation device that presents a tactile sensation to the user.

The functional configuration example of the output control device 30 according to the embodiment of the present disclosure has been described above.

[2.5. Function Details of Control of Internal State]

Next, function details of the control of the internal state will be described.

(2.5.1. Various Physiological Index Values)

As described above, the sensor unit 330 included in the output control device 30 may include at least one of a peripheral bloodstream sensor, an electrocardiographic sensor, a pulse sensor, or a perspiration sensor. In addition, as described above, the sensor unit 230 included in the display device 20 may include a brain wave sensor. Hereinafter, examples of physiological index values detected by these sensors will be described.

FIG. 6 is a diagram illustrating examples of physiological index values detected by various sensors. As illustrated in FIG. 6, the peripheral bloodstream sensor (a bloodstream around a skin) detects physiological index values such as a change in a blood flow volume, a bloodstream ratio of an arteriole to a capillary, and a bloodstream ratio of a face to a hand. In addition, the heartbeat (pulse) sensor detects physiological index values such as a heart rate and heartbeat variability. In addition, the perspiration sensor detects a physiological index value such as palm perspiration (including a wrist). In addition, the brain wave sensor detects a physiological index value such as a frequency component for each electrode.

In addition, as illustrated in FIG. 6, contraction of an arteriole obtained from a change in a blood flow volume has correlation with sympathetic nerve activity reaction. In addition, a change in a cardiac output obtained from a change in a blood flow rate has correlation with sympathetic nerve activity reaction. However, the change in the cardiac output is also considerably made by an exercise. Therefore, when the change in the cardiac output is used alone as a sympathetic nerve index, precision is low. The contraction of an arteriole obtained from a bloodstream rate of the arteriole to a capillary has correlation with sympathetic nerve activity reaction. A pattern of the contraction of an arteriole obtained from a bloodstream rate of a face to a hand has correlation with sympathetic nerve activity reaction and parasympathetic nerve activity reaction.

Adjustment of a cardiac output obtained from a heart rate has correlation with sympathetic nerve activity reaction. However, the adjustment of the cardiac output is also considerably changed by an exercise. Therefore, when the adjustment of the cardiac output is used alone as a sympathetic nerve index, precision is low. Blood pressure-related Variability obtained from heartbeat variability has correlation with sympathetic nerve activity reaction and parasympathetic nerve activity reaction. Respiration-related variability obtained from heartbeat variability has correlation with sympathetic nerve activity reaction. Mental perspiration obtained from palm perspiration has correlation with sympathetic nerve activity reaction. A frequency component for each electrode of the brain wave sensor has correlation with the degree of activity of each part in a brain.

The examples of the physiological index values detected by the various sensors have been mainly described above.

(2.5.2. Physiological Index Space)

In this way, the biosensors such as the sensor unit 330 included in the output control device 30 and the sensor unit 230 or the like included in the display device 20 can each detect physiological index values corresponding to the biosensors. Here, the foregoing physiological index values have correlation with at least one of sympathetic nerve activity reaction or parasympathetic nerve activity reaction. Accordingly, one physiological index value and a combination of the plurality of physiological index values can be plotted to one position in a physiological index space that has the degree of sympathetic nerve activity and the degree of parasympathetic nerve activity as axes.

Note that in the present specification, a case in which the physiological index space is a 2-dimensional space that has the degree of sympathetic nerve activity and the degree of parasympathetic nerve activity as axes will be mainly described. However, the physiological index space is not limited to the 2-dimensional space that has the degree of sympathetic nerve activity and the degree of parasympathetic nerve activity as axes. For example, the physiological index space may be a 3-dimensional space that has three axes. That is, it is sufficient if the physiological index space is a multi-dimensional space that has a plurality of axes.

Hereinafter, a position of the physiological index space corresponding to one physiological index value or a combination of a plurality of physiological index values is also referred to as a "state point" in the physiological index space. In addition, hereinafter, a case in which a state point corresponding to a physiological index value detected by the sensor unit 230 included in the display device 20 are used will be mainly described. However, state points corresponding to a plurality of physiological index values may be used. For example, a state point corresponding to a combination of a physiological index value detected by the sensor unit 230 included in the display device 20 and a physiological index value detected by the sensor unit 330 included in the output control device 30 may be used.

The physiological index space has been mainly described above.

(2.5.3. Feedback in Accordance with Change in State Point)

As described above, it is important for users to be able to control their internal state to some extent in various occasions. Accordingly, in the present specification, in the output control device 30, the data acquisition unit 311 acquires a physiological index value detected by the sensor unit 330 and the processing unit 312 calculates a state point in the physiological index space corresponding to the physiological index value. Then, the output control unit 313 controls output of output information in accordance with a change in the state point in the physiological index space corresponding to the physiological index value.

In the configuration, when the user views the output information, the user can learn a method of controlling the internal state. Therefore, the user can be expected to be able to control his or her internal state more easily.

More specifically, the processing unit 312 may calculate a reward value on the basis of a change in the state point in the physiological index space. The output control unit 313 may acquire the reward value and control the output of the output information in accordance with the reward value. In this way, by calculating the reward value from the change in the state point in the physiological index space and generating the output information in accordance with the reward value, it is possible to generate more appropriate output information.

(2.5.4. Mental Stretch Training)

Here, a target internal state of the user may be set or may not be set. For example, when a physiological index values for calculating a state point of the user with high precision are detected, a target internal state is not particularly set. At this time, it is sufficient if the output control unit 313 controls output of an alert only in a case in which the internal state of the user approaches an inappropriate internal state. First, a case in which the target internal state of the user is not set will be described. In the case in which the target internal state of the user is not set, output information to be output is not limited.

As one method of supplying output information meaningful to the user without setting the target internal state, output of information for performing training in which the user is caused to transition the internal state in a larger range can be exemplified. Specifically, the processing unit 312 further increases a reward value in a case in which the state point transitions to a position at which a distribution density of previous state points is lower. In this case, the reward value increases in a case in which a change of the state point deviating from the previous distribution is shown. In this case, for example, in a case in which the user is sad more strongly, is pleased more strongly, or concentrates more strongly than was previously, the internal state reaches a state point which the internal state has not reached previously. Therefore, the reward value calculated by the processing unit 312 on the basis of the distribution of the previous state points increases. When the user receives feedback of such a reward value, the user can perform training so that the user can enjoy a richer emotional experience. Hereinafter, such training is referred to as "mental stretch training." In this case, it is sufficient if the output control unit 313 controls output of the output information in accordance with distribution density of previous state points using current state points in the physiological index space as a standard.

Figure 7:
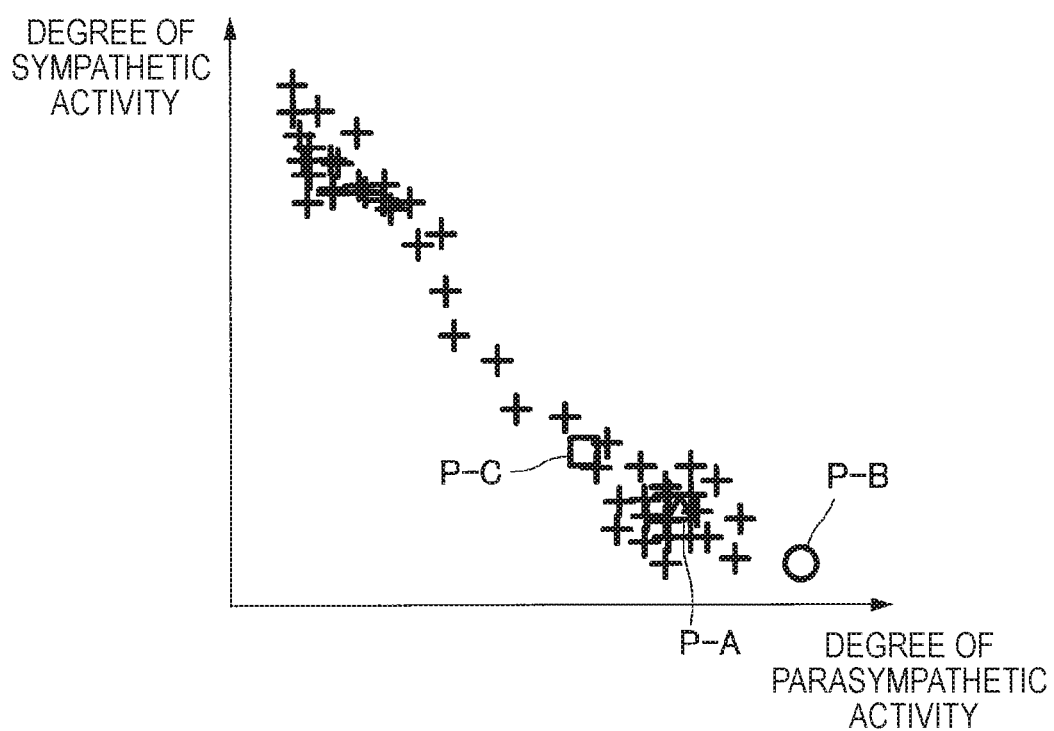
FIG. 7 is an explanatory diagram illustrating output information in accordance with distribution density of previous state points for which a current state point serves as a standard.

FIG. 7 is an explanatory diagram illustrating output information in accordance with distribution density of previous state points for which a current state point serves as a standard. Referring to FIG. 7, a distribution of previous state points is indicated by a sign +.

Here, a current state point is located at one of a point P-A, a point P-B, and a point P-C.

In a case in which the current state point is located at the point P-A indicated by a sign Δ, the distribution density of the previous state points for which the current state point serves as the standard is the maximum in the space. Accordingly, in this case, it is sufficient if the output control unit 313 controls the output of the corresponding output information in a case in which the distribution density of the previous state points for which the current state point serves as the standard is the maximum. An example of specific output information will be described later.

On the other hand, in a case in which the current state point is located at the point P-B indicated by a sign O, the distribution density of the previous state points for which the current state point serves as the standard is 0. Accordingly, in this case, it is sufficient if the output control unit 313 controls the output of the corresponding output information in a case in which the distribution density of the previous state points for which the current state point serves as the standard is 0. An example of specific output information will be described later.

On the other hand, in a case in which the current state point is located at the point P-C indicated by a sign □, the distribution density of the previous state points for which the current state point serves as the standard is an intermediate value between the maximum value and 0 in the space. Accordingly, in this case, it is sufficient if the output control unit 313 controls the output of the corresponding output information in a case in which the distribution density of the current state points is an intermediate value between the maximum value and 0. An example of specific output information will be described later.

When the user perceives such output information, the user easily orients a more stretched (considerably changed) internal state by the principle of biofeedback. In addition, the user can learn to orient the more stretched (considerably changed) internal state. An example of specific output information will be described later.

As another method of supplying output information meaningful to the user without setting the target internal state, there is a method of performing output in accordance with a transition speed of a state point to train for causing the position of the state point to transition quickly. As still another method of supplying output information meaningful to the user without setting the target internal state, there is a method of performing output in accordance with the magnitude of a fluctuation range of the position of a state point to train narrowing the fluctuation range of the position of the state point. In this method, the output may be controlled using an average value of transition speeds of previous state points (for example, previous state points located within a predetermined distance) located nearby the current state point serving as the standard or an average value of the fluctuation range of previous state points (for example, previous state points located within a predetermined range) located nearly the current state point serving as the standard. On the other hand, even in a case in which the target internal state is set, the control of the output based on the transition speed and the fluctuation range is useful. Therefore, in the present disclosure, an example in which output is controlled on the basis of a transition speed of a state point and a fluctuation range of the state point will be described giving an example of a case in which the target internal state is set.

In a case in which the target internal state is not set, the following advantageous effects can be obtained. First, the advantageous effect that it is not necessary to designate an optimum value of a physiological index in advance is obtained. Here, an ability to cause an internal state to be changed within a larger range leads to an improvement in adaptability to an environment and a situation. In addition, an ability to cause an internal state to be changed more quickly leads to an improvement in a capacity to adapt to an environment and a situation in a short time. In addition, an ability to cause an internal state to be maintained more stably increases an ability to continue adaptation appropriately.

In addition, an individual difference in a physiological index is large. Even when a specific state value is designated, it may not be said to necessarily guide the user to an optimum internal state. However, by improving the foregoing abilities, the user can improve an ability to control his or her internal state irrespective of what each physiological index value means. Further, since the user can continue to use the system enjoying a value by an index which does not depend on a specific state value, it is sufficient if precise discrimination of a preferable internal state of the user is learned using a state value obtained when the system is used.

The mental stretch training has been mainly described above.

(2.5.5. Mental Stretch Training Using Content Appreciation)

The mental stretch training in the method of presenting only output information to the user has been described above. Hereinafter, a case in which various internal states of the user are guided using content appreciation will be mainly described. For example, presentation of content which the user is allowed to view urges the user to experience various internal states. Physiological index values are detected by the biosensors while content is output. When the content is output, various internal states are easily aroused.

In addition, a kind of content is not particularly limited. For example, the content may include virtual reality (VR) content configured using VR. Then, since the user can enjoy the feeling of presence more strongly, each internal state is expected to be aroused more strongly. The content may be game content, may be appreciation content (for example, a movie or the like), or may be relaxing content (for example, a landscape video or the like). The mental stretch training is not training to guide the user to a specific target value. For example, when the user appreciates content for arousing a specific internal state, training for experiencing the specific internal state more deeply can be performed.

For example, in a case in which the user appreciates appreciation content, it is sufficient if the user immerges in the appreciation content consciously and is aware of feelings clearly. In addition, in a case in which the user views game content, it is sufficient if the user immerges in the game content consciously and is aware of maintaining high concentration. In addition, in a case in which the user views relaxing content, it is sufficient if the user is released from tension in the game content consciously and is aware of maintaining deep relaxing. Hereinafter, training for being aware of orienting an individual internal state to a deeper internal state while appreciating content is also referred to as "mental stretch training using content appreciation."

The user may be allowed to view one kind of content, but it is preferable to allow the user to view a plurality of kinds of content. Thus, a plurality of internal states of the user may be aroused to correspond to the plurality of kinds of content. In addition, by switching and output the plurality of kinds of content, the user can be caused to transition his or her internal state in a larger range. Thus, the internal state can be caused to transition more quickly and the plurality of internal states can be maintained more stably.

Figure 8:
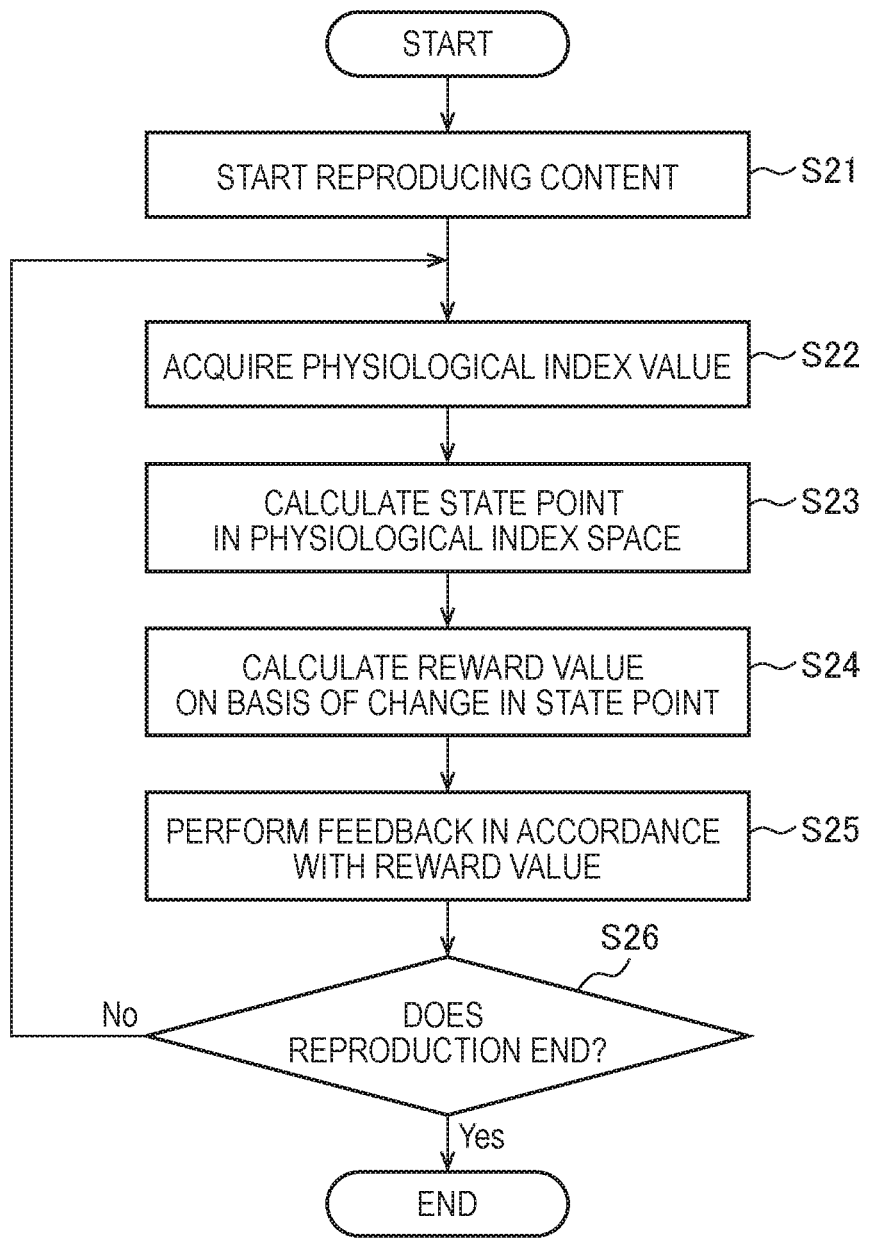
FIG. 8 is a flowchart illustrating an example of an operation of mental stretch training.

FIG. 8 is a flowchart illustrating an example of an operation of mental stretch training. Note that the flowchart illustrated in FIG. 8 is merely an example of an operation of the mental stretch training. Accordingly, the operation of the mental stretch training is not limited to the example of the operation of the flowchart illustrated in FIG. 8.

As illustrated in FIG. 8, when the generation unit 112 in the information processing device 10 starts reproducing content (S21), the display unit 260 in the display device 20 outputs the content. The user appreciates the content output in this way. Then, while the user is viewing the content, the sensor unit 330 in the output control device 30 detects a physiological index value.

When the data acquisition unit 311 in the output control device 30 acquires the physiological index value (S22), the processing unit 312 calculates a state point in the physiological index space corresponding to the physiological index value (S23). The processing unit 312 calculates a reward value on the basis of a change in the state point (S24). Here, as the change in the state point, distribution density of the previous state points for which the current state point serves as a standard, a transition speed of the state point, stability of the state point, and the like can be exemplified. Then, the output control unit 313 performs feedback in accordance with the reward value (output control of the output information in accordance with the reward value) (S25).

In a case in which the reproduction of the content continues ("No" in S26), the control unit 310 returns the process to S22. Conversely, in a case in which the reproduction of the content ends ("Yes" in S26), the control unit 310 ends the operation. The calculation of the reward value based on the change in the state point and the feedback in accordance with the reward value have been described above in "2.5.3. Feedback in accordance with change in state point."

Through the mental stretch training, the following advantageous effects are obtained. First, the advantageous effect that the user can develop the ability to make various internal states inside as well as specific internal states is obtained. In addition, through the mental stretch training, the user can expand a range in which the internal state is caused to be changed, improve the stability of the internal state, and improve the transition speed of the internal state. Through the mental stretch training, it is possible to arouse the various internal states using the content.

In addition, as described above, a preferred internal state for the user can also be set through the feedback from the user through the mental stretch training. In addition, as will be described below, labeling occurs at the state point on the basis of a correspondent relation between a label assigned to the content and the state point corresponding to the internal state of the user even through mental stretch training using content. That is, through the label included in the content and the feedback from the user, learning for improving internal state determinability is possible during training in which a value is supplied.

Further, even in an internal state for which determination is ambiguous, it is possible to supply a valuable training method through the mental stretch training.

The mental stretch training has been described above.

(2.5.6. Unsupervised Individualization Learning)

Next, individualization learning will be described. First, a plurality of state points of an internal state of the user is accumulated over time. When machine learning is performed on the plurality of state points accumulated in this way, a tendency of the internal state of the user is learned for each individual. Accordingly, the machine learning for the plurality of state points of the user accumulated over time will be described. Note that the machine learning for the plurality of state points of the user is not compulsory. Herein, unsupervised machine learning will be described as an example of the machine learning.

Figure 9:
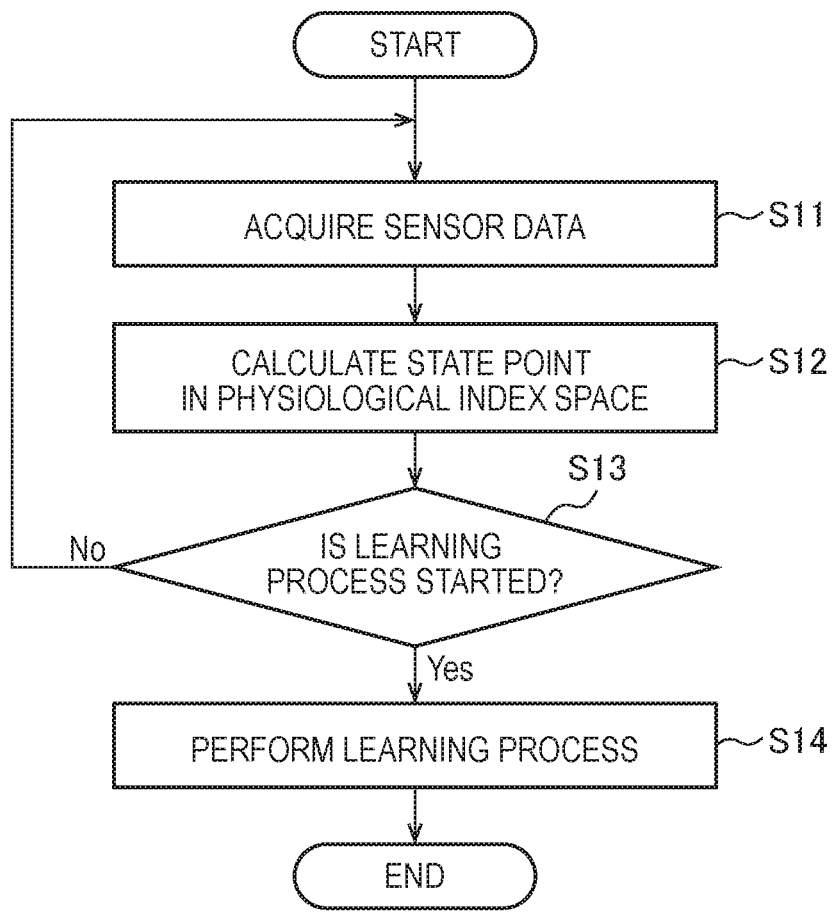
FIG. 9 is a flowchart illustrating an example of a flow of an operation of machine learning for a plurality of state points.

FIG. 9 is a flowchart illustrating an example of a flow of an operation of machine learning for a plurality of state points. As illustrated in FIG. 9, the physiological index value detected by the output control device 30 is transmitted to the information processing device 10. The acquisition unit 111 in the information processing device 10 acquires the physiological index value (S11) and the generation unit 112 calculates a state point in the physiological index space corresponding to the physiological index value (S12). A plurality of state points of the user is calculated by performing the calculation of the state point a plurality of times.

Before the generation unit 112 starts machine learning on the plurality of state points ("No" in S13), the process transitions to S11. Conversely, in a case in which the generation unit 112 starts the machine learning on the plurality of state points ("Yes" in S13), the generation unit 112 starts the machine learning on the plurality of state points (S14). Through the machine learning by the generation unit 112, the plurality of state points in the physiological index space are classified into a plurality of clusters.

Note that in a case in which the user feels a bothering state point (for example, a state point on which the user concentrates), feeling his or her internal state, the user may input information indicating the internal state. In this case, when the manipulation unit 320 receives the information indicating the internal state from the user, the processing unit 312 may associate the information indicating the internal state with a current state point. When the information indicating the internal state is used as a label in the machine learning, the information indicating the internal state can be associated with the current state point (and the cluster to which the current state point belongs) and the bothering state point (or the cluster to which the bothering state point belongs) can be selected as a transition source state or a transition destination state.

The unsupervised individualization learning has been mainly described above.

(2.5.7. Supervised Individualization Learning)

The unsupervised individualization learning has been described above. That is, the example in which the plurality of state points in the physiological index space are classified into the plurality of clusters through the machine learning has been described. However, when the user can be caused to appreciate content, machine learning can also be performed using a label added to the content as a supervised signal. At this time, in the information processing device 10, the generation unit 112 associates a label added to content output at a tuning in accordance with detection of a corresponding physiological index value to each of the plurality of clusters.

Through the machine learning, it is possible to associate the label with a state value cluster to which a meaning has not been given until then. In addition, for example, by associating the label (an index for arousing an internal state) with each scene of movie content using a phased numerical value, it is possible to perform machine learning for ascertaining an internal state using continuous numerical values.

At this time, in a case in which evaluation information of content (for example, also including appreciation or the like on content) is input from the user, the label can be corrected on the basis of the evaluation information and the machine learning can also be used using the corrected label as a supervised signal. That is, the generation unit 112 may correct the label on the basis of the evaluation information of the content input from the user. Through the correction, it is possible to perform more appropriate machine learning.

For example, in a case in which the user inputs first evaluation information (appreciation indicating a rich emotion) such as "interesting," "excited," or "moved to tears," it is sufficient if the label is corrected to a low or high extreme value. On the other hand, in a case in which the user inputs appreciation (second evaluation information) indicating a monotonous emotion such as "boring" or "dull," it is sufficient if the label is corrected to an average value.

In addition, as described above, an internal state preferable for the user can be set by feedback from the user even in the supervised machine learning. In addition, the machine learning may be performed for a plurality of users in advance and learning results obtained in the machine learning performed for the plurality of users may be preset.

FIG. 10 is an explanatory diagram illustrating an example of association of labels with state points. Referring to FIG. 10, content IM-1 is output at times T11 to T18. On the other hand, content IM-2 is output at times T21 to T28. The content IM-1 is game content and a concentration state of the user can be aroused when the user views the content. On the other hand, the content IM-2 is relaxing content and a relaxed state of the user can be aroused when the user views the content.

The generation unit 112 associates the label added to the content output at a timing in accordance with detection of a corresponding physiological index value with each of the plurality of state points. For example, a label "concentration" added to the content IM-1 output at timings (times T11 to T18) at which corresponding physiological indexes are detected can be associated with state points E11 to E18. On the other hand, a label "relaxing" added to the content IM-2 output at timings (times T21 to T28) at which corresponding physiological indexes are detected can be associated with state points E21 to E28.

Figure 11:
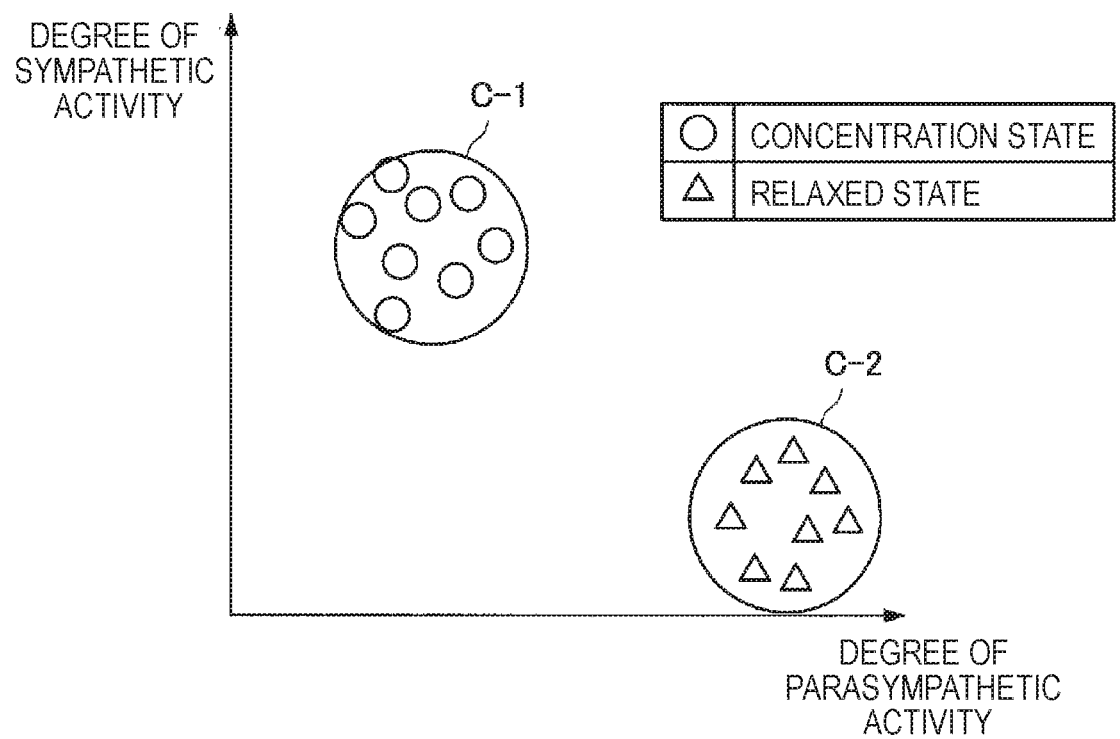
FIG. 11 is a diagram illustrating an example of a label associated with each of a plurality of clusters.

FIG. 11 is a diagram illustrating an example of a label associated with each of a plurality of clusters. A label indicating a concentration state can be associated with a cluster C-1. A label indicating a relaxed state is associated with a cluster C-2. In this way, by associating the label added to the content output at the timings in accordance with detection of the corresponding physiological index value with each of the plurality of state points, it is possible to associate an appropriate label with each of the plurality of clusters.

Figure 12:
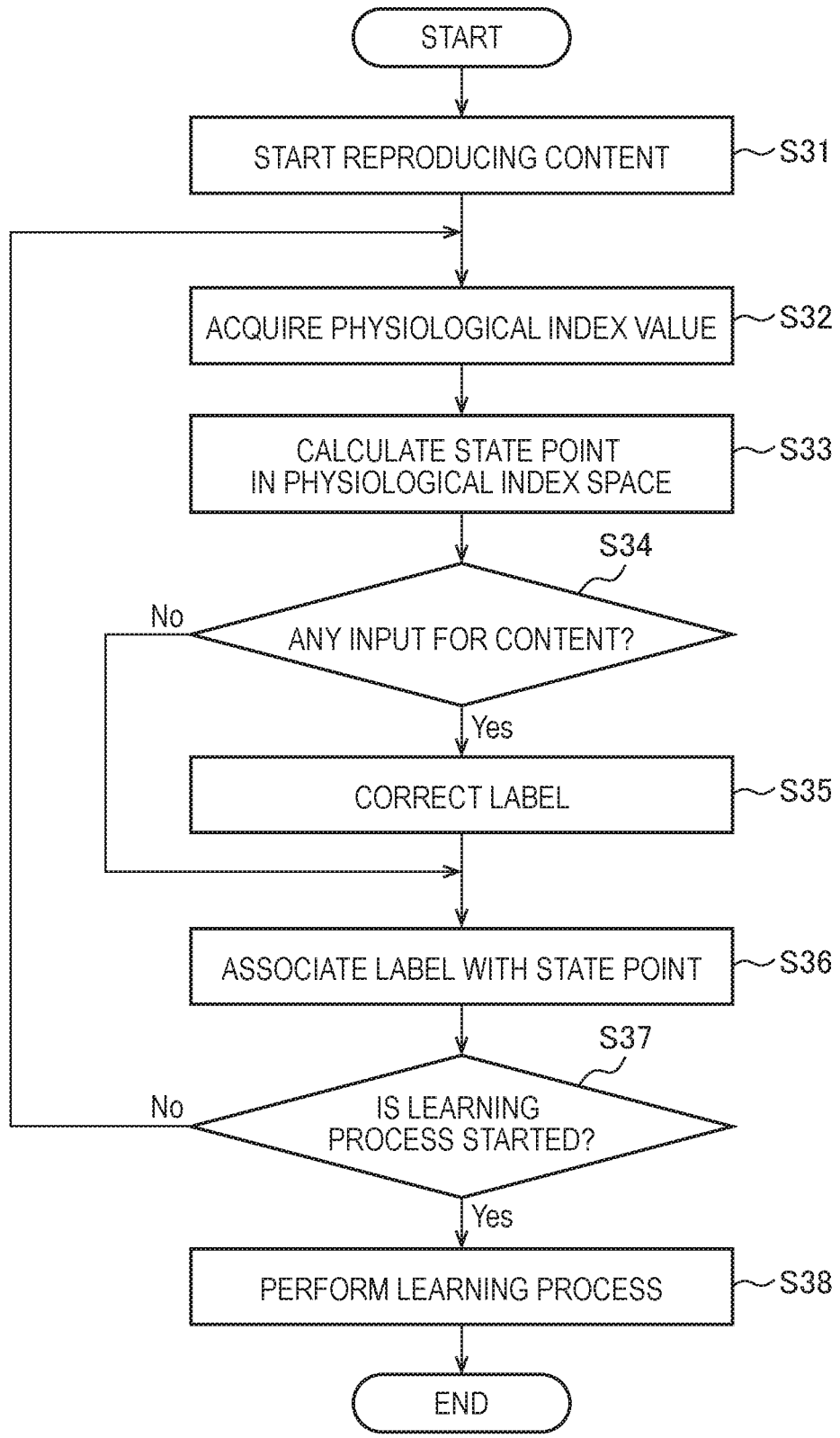
FIG. 12 is a flowchart illustrating an example of a flow of an operation of supervised machine learning.

FIG. 12 is a flowchart illustrating an example of a flow of an operation of supervised machine learning. As illustrated in FIG. 12, when the generation unit 112 in the information processing device 10 starts reproducing content (S31), a physiological index value detected by the output control device 30 is transmitted to the information processing device 10. In the information processing device 10, the acquisition unit 111 acquires the physiological index value (S32) and the generation unit 112 calculates a state point in the physiological index space corresponding to the physiological index value (S33). The plurality of state points of the user can be calculated by performing the calculation of the state points a plurality of times.

In a case in which there is no input of evaluation information of the content ("No" in S34), the generation unit 112 causes the process to proceed to S36. Conversely, in a case in which there is an input of evaluation information of the content ("Yes" in S34), the generation unit 112 corrects the label (S35) and causes the process to proceed to S36. The generation unit 112 associates the label with the state point (S36) and causes the process to transition to S32 until the machine learning of a plurality of state points starts ("No" in S37). Conversely, in a case in which the generation unit 112 starts the machine learning for the plurality of state point ("Yes" in S37), the generation unit 112 starts the machine learning for the plurality of state point (S38). Through the machine learning by the generation unit 112, the label is associated with each of the plurality of clusters.

Note that since a state point group corresponding to a section of a predetermined time immediately after switch of the content or the label assigned by the input of the user is treated as a different internal state from the assigned label, precision of the machine learning can be further improved by assigning a flag indicating that state transition is in progress.

The supervised individualization learning has been mainly described above.

(2.5.8. Mental Switch Training)

The example in which the various internal states are aroused with the content has been described above. On the other hand, efficient transition between desired internal states is also one desire of the user. For example, a case in which the user concentrates for work hours and desires to be relaxed quickly during a rest time, or the like corresponds to the desire. Hereinafter, training for obtaining an ability to efficiently switch an internal state between the transition source state and the transition destination state designated in this way is also referred to as "mental switch training." Significance of designation of the transition destination state by the user will be described below.

In general, it is known that there is a person who has a routine in which he or she takes a deep breath at a tension time and is relaxed. Such a routine can be said to be a good way of escaping from a tension. However, a relaxed state and a concentration state are internal states considerably away from the activity state space of autonomic nerves. Therefore, to improve concentration from an internal state relaxed for a moment, some time may be necessary. Shortening the transition time is beneficial to a user who desires to escape from tension for a short time and concentrate. On the other hand, a tension state and a concentration state are known to be either an internal state in which sympathetic nerve activity is stimulated. A distance between both the tension state and the concentration state in an internal state space is closer than a distance to a relaxed state. Since the distance between both the tension state and the concentration state is close, there is a possibility of transition in a short time. However, since it is difficult for the user to detect the transition of the internal state, there is a problem that it is difficult to escape from tension psychologically.

As described above, a desire of the user is direct transition from a tension state to a concentration state. Accordingly, it is sufficient if a way capable of directly transitioning between different internal states quickly is applied. Here, in a case in which transition from a tension state to a concentration state is considered, an internal state distant from the tension state in the range of the concentration state may be selected as a transition destination state. It is easy to transition to an internal state distant from the tension state more intentionally and it is easy for the user to detect the transition. In addition, since the concentration state is not distant from the tension state as the relaxed state, the concentration state can transition in a short time.

In addition, a way of switching the internal state to concentration using a certain regular behavior (including a thinking as an opportunity. Therefore, it is sufficient if the user performs a regular behavior for arousing certain concentration as well at the time of the mental switch training. Thus, the user easily orient the internal state to concentration using a behavior which the user perform voluntarily as an opportunity (in a performance, it is possible to improve a success ratio of switching of an internal state).

In addition, through learning by the user, a tendency to increase a distance between a tension state and a concentration state can also occur. Thus, the user can perform transition of the internal state from the tension state to the concentration state more easily, and thus can maintain high-quality concentration more away from tension.

The significance of the designation of the transition destination state by the user has been described above. In the mental switch training, the transition source state and the transition destination state is enabled to be designated by the user. For example, in a case in which the user feels a tension state before an important presentation, the user may input the point of time. Thus, the information processing device 10 can learn a state point of the user at the point of time as a transition source state. In addition, when the user has a rehearsal and feels the concentration state, the information processing device 10 can learn the state point of the user at the point of time as a transition destination state by inputting the point of time.

When the user feels the transition source state, it is sufficient if the user practices switching to the transition destination state, receiving biofeedback. At this time, for example, "to make an uneasy internal state consciously" is work with high psychological load, and therefore is not a preferable experience for the user. On the other hand, to reproduce uneasiness by causing the user to view content for arousing the uneasiness again among content previously viewed by the user is work with relatively low psychological load for the user. Accordingly, at the time of practice, content may be viewed to make a transition source state.

In addition, in a case in which a distance between a transition source state and a transition destination state is relatively close, for example, an internal state distant from the center of a cluster to which the transition source state belongs within the cluster of the transition destination state may be targeted. Thus, it is easy for the user to be aware of a physiological difference between both the internal states, and thus it is possible to improve a success ratio of learning by biofeedback. In addition, a state point selected as a target in such a way does not necessarily correspond to a best internal state (for example, the state point is not necessarily an internal state at the time of most concentration). However, since the state point can be distant from a tension state, the state point is suitable as a transition destination state. By changing the internal state to the internal state selected as a target in this way, it is easy for the user to detect a change in his or her internal state. Therefore, the detection of the change is an opportunity to induce a change in a psychological state as well.

Figure 13:
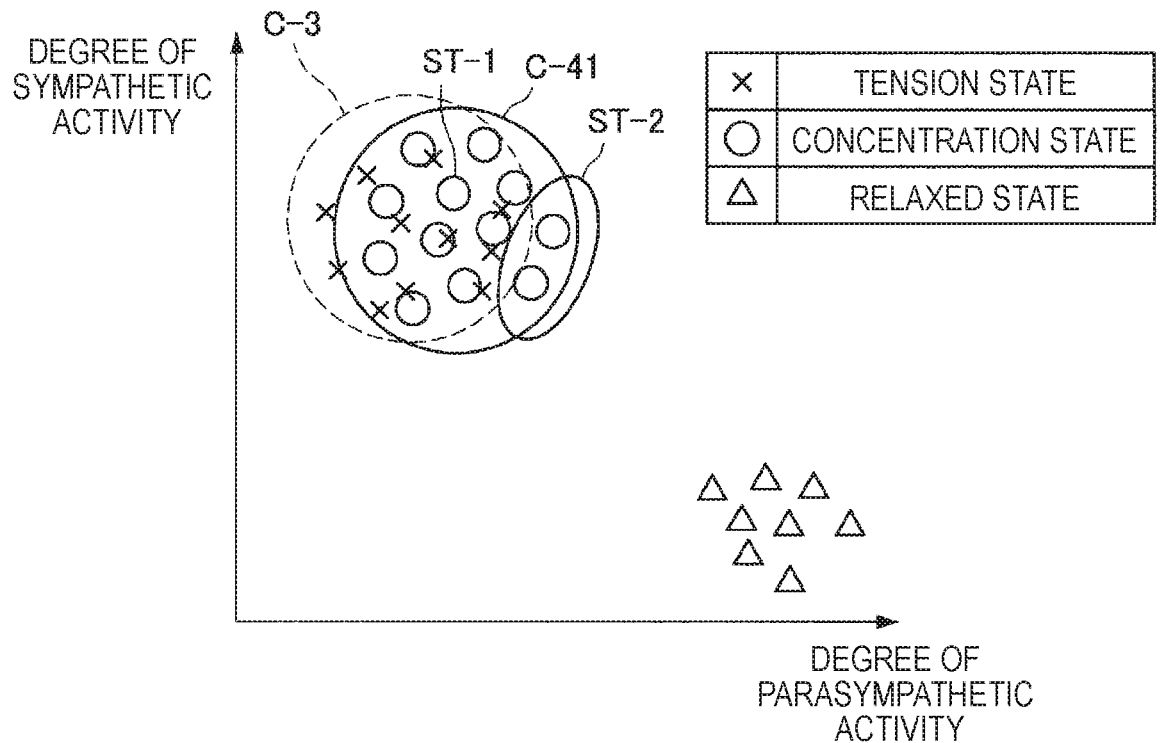
FIG. 13 is an explanatory diagram illustrating an example in which a transition destination state is selected.
Figure 14:
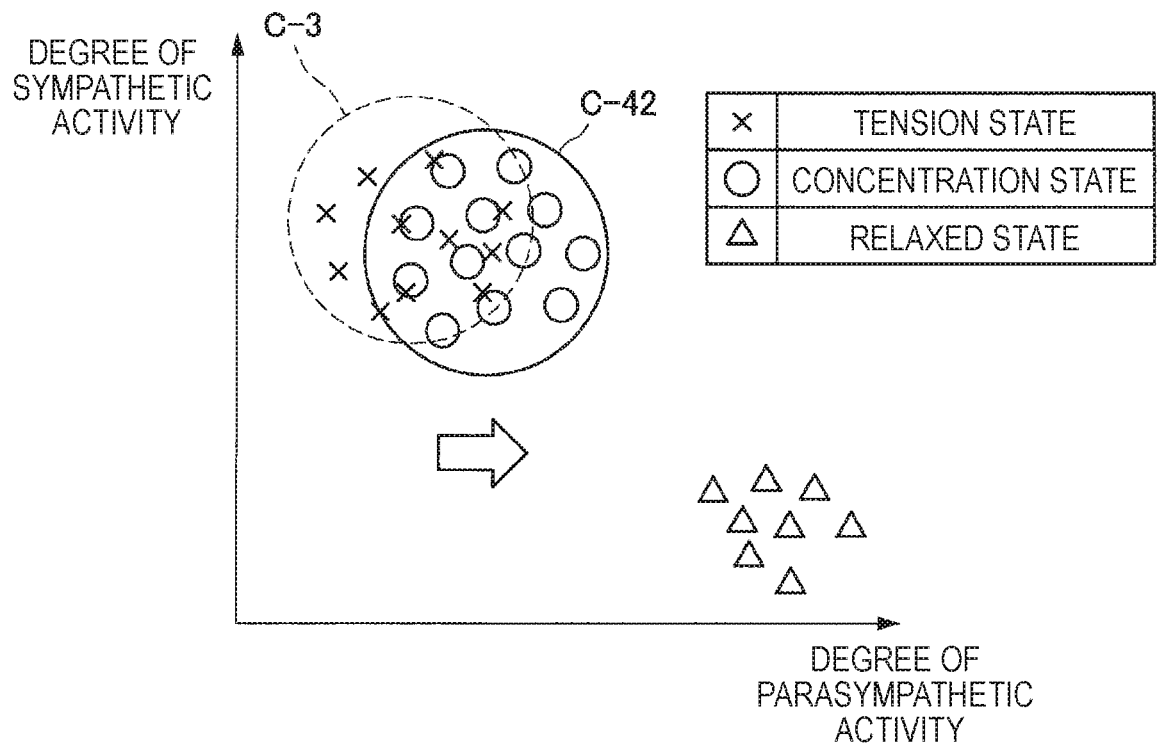
FIG. 14 is an explanatory diagram illustrating an example in which a transition destination state is selected.

FIGS. 13 and 14 are explanatory diagrams illustrating examples in which transition destination states are selected. Referring to FIGS. 13 and 14, a tension state, a concentration state, and a relaxed state are illustrated. A cluster C-41 is a cluster to which a plurality of concentration states belongs and a cluster C-3 is a cluster to which a plurality of tension states belongs. A state point ST-1 indicates a concentration state in which the user feels most appropriate. Accordingly, in a case in which the transition source state is assumed to be a tension state and the transition destination state is assumed to be a concentration state, it is considered that it is preferable to designate the state point ST-1 as the transition destination state.

However, for the transition destination state, because of the above-described reason, an internal state which is most distant from the center of the cluster C-3 corresponding to the tension state may be selected as the transition destination state in the cluster C-41 corresponding to the concentration state. In addition, by selecting such a transition destination state, the user can learn the transition to the concentration state of the physiological state distant from the tension state and stably maintain the state point of the concentration state of a physiological state distant from the tension state. Thus, a tendency for the cluster of the tension state to be distant from the cluster of the concentration state can occur. Referring to FIG. 14, it is ascertained that a cluster C-42 corresponding to the concentration state after learning by the user is distant from the cluster C-3 corresponding to the tension state. Thus, the user can perform internal state transition from the tension state to the concentration state more easily.

In the mental switch training, the user is expected to be able to control the internal state so that the internal state transitions more quickly. To support the learning of the user, the processing unit 312 may further increase the reward value in a case in which the transition speed of the state point in the physiological index space is higher. For example, in a case in which the user performs concentration quickly or performs relaxing quickly, the processing unit 312 increases the reward value because the internal state transitions quickly. In this case, it is sufficient if the output control unit 313 controls output of the output information in accordance with the transition speed of the state point in the physiological index space.

The processing unit 312 may calculate the transition speed of the state point in any way. For example, in a case in which the user causes the state point to transition, the transition speed may be calculated to be higher as a time taken to perform transition of the state point of the user from a state point of a transition source to a state point of a transition destination is shorter. A timing of each of the state points of the transition source and the transition destination may be designated by the user, the processing unit 312 may automatically recognize a transition start time and a transition end time of the state point, and the state point of each of the transition start time and the transition end time may be designated as the state point of each of the transition source and the transition destination.

Alternatively, in a case in which a state point transitions between two different clusters, the processing unit 312 may set a time taken for the transition of the state point from the inside of the cluster of the transition source to the inside of the cluster of the transition destination as a transition speed. In the present specification, a case in which two different clusters are formed from previous state points of the user himself or herself will be mainly assumed. However, at least one of the two different clusters may be formed from state points of other users measured in advance (for example, clusters or the like of other users in which attributes of the users are similar). The attributes may be sex, age, and the like.

Figure 15:
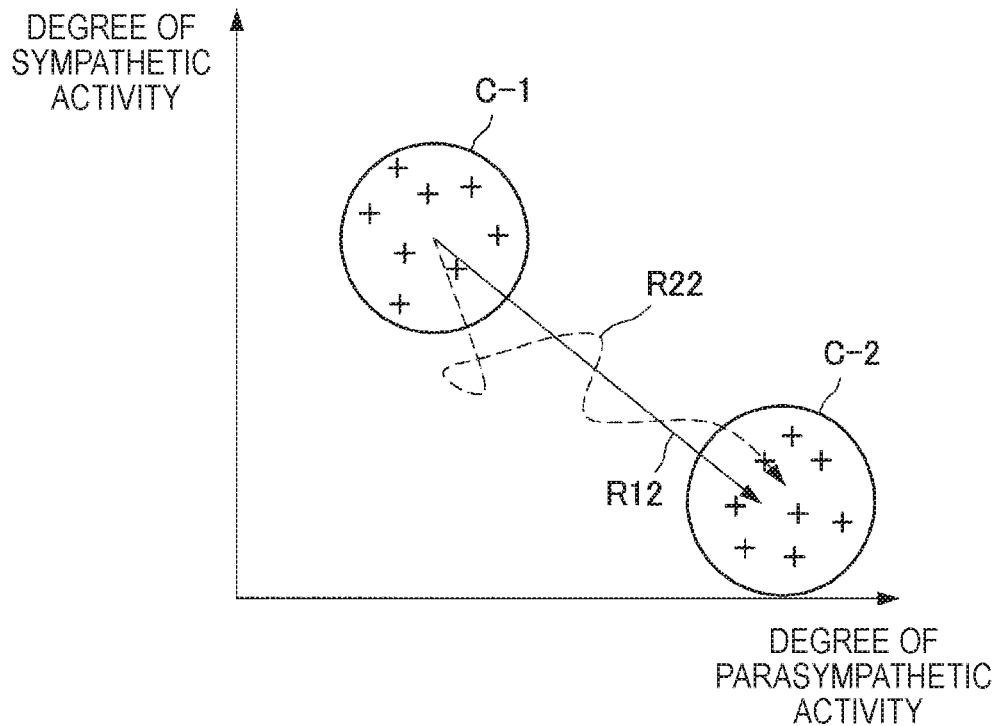
FIG. 15 is an explanatory diagram illustrating output information in accordance with a transition speed of a state point in a physiological index space.

FIG. 15 is an explanatory diagram illustrating output information in accordance with a transition speed of a state point in a physiological index space. Referring to FIG. 15, previous state points are classified into the cluster C-1 and the cluster C-2. The cluster C-1 and the cluster C-2 can be formed through machine learning, but the machine learning may not be performed. In addition, labeling is performed on the state points in any method and the clusters may be formed on the basis of the label values.

Where a state point of the transition source of the user is located is not limited. Here, a case in which the state point of the transition source of the user is inside the cluster C-1 is assumed. Here, a case in which the state point transitions to the inside of the cluster C-2 along a route R-12 in a short time and a case in which the state point transitions to the inside of the cluster C-2 along a route R-22 for a long time are assumed.

In a case in which the state point transitions to the inside of the cluster C-2 along the route R-12 in a short time, a transition speed of the state point is assumed to be greater than a predetermined threshold. In this case, it is sufficient if the output control unit 313 controls output of output information indicating that the transition speed of the state point is greater than the threshold. As the predetermined threshold, for example, a value or the like obtained by multiplying an average value of previous transition speeds between the clusters C-1 and C-2 by a constant may be used.

The user receives quantitative feedback related to the transition speed of the internal state, and thus it is easy to perform the transition of the internal state performed currently more quickly by a principle of the biofeedback. In addition, the user can learn to cause the internal state to transition more quickly. An example of specific output information will be described later.

On the other hand, in a case in which the state point transitions to the inside of the cluster C-2 along the route R-22 for a long time, the transition speed of the state point is assumed to be less than the predetermined threshold. In this case, it is sufficient if the output control unit 313 controls output of output information indicating that the transition speed of the state point is less than the predetermined threshold. An example of specific output information will be described later.

In the mental switch training, the user is expected to be able to control the internal state so that the internal state is further stabilized. To support the learning of the user, the processing unit 312 may further increase the reward value in a case in which the stability of the state point in the physiological index space is higher. For example, in a case in which the user does not consume all the concentration or does not distract relaxation, the processing unit 312 increases the reward value because the internal state can be stabilized. In this case, it is sufficient if the output control unit 313 controls output of the output information in accordance with the stability of the state point in the physiological index space.

The processing unit 312 may calculate the stability of the transition speed of the state point in any way. For example, as the magnitude of a fluctuation range of the state point of the user within a predetermined time is smaller, the stability may be calculated to be higher. Alternatively, in a case in which the user causes the state point to transition, the stability may be calculated to be higher as the magnitude of the fluctuation range of the state point at the transition destination within a predetermined time is smaller.

At this time, since it is considered that it is more difficult to stabilize the state point at the transition destination as the transition distance of the state point is greater, the processing unit 312 may normalize the stability by using a coefficient in accordance with the magnitude of the transition distance of the state point. More specifically, the processing unit 312 may normalize the stability by multiplying the stability by a larger coefficient as the latest transition distance of the state point is greater.

On the other hand, in a case in which a distance between the cluster to which the current state point belongs and a neighboring cluster is close, switch to the latest internal state occurs with smaller fluctuation than in a case in which the distance is long. Therefore, in a case in which the user is stabilized and remains in a certain internal state, it is preferable to output the fluctuation of the state point more acutely as the distance with the neighboring cluster is closer. Accordingly, the processing unit 312 may normalize the stability by using a coefficient in accordance with a distance from the state point of the transition destination to the closest cluster. More specifically, the processing unit 312 may normalize the stability by multiplying the stability by a larger coefficient as the distance from the state point of the transition destination to the closest cluster is shorter.

In addition, in the present specification, a case in which two different clusters are formed by previous state points of the user himself or herself is mainly assumed. However, at least one of the two different clusters may be formed from the state points of other users (for example, clusters or the like of other users in which attributes of the users are similar).

Figure 16:
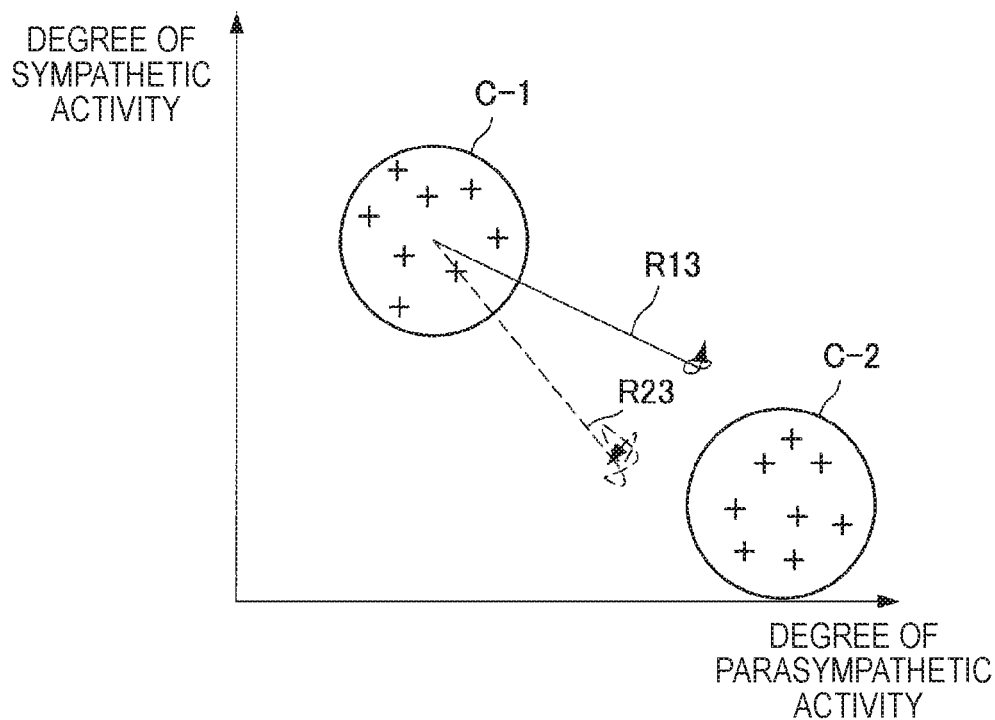
FIG. 16 is an explanatory diagram illustrating output information in accordance with stability of a state point in a physiological index space.

FIG. 16 is an explanatory diagram illustrating output information in accordance with stability of a state point in a physiological index space. Referring to FIG. 16, previous state points are classified into the cluster C-1 and the cluster C-2. Note that, as in the example described with reference to FIG. 15, the cluster C-1 and the cluster C-2 can be formed through machine learning, but the machine learning may not be performed.

As in the example described with reference to FIG. 15, where a state point of the transition source of the user is located is not limited. Here, a case in which the state point of the transition source of the user is inside the cluster C-1 is assumed. Here, as a result obtained when the user attempts transition of a state point to the cluster C-2, a case in which the state point is stabilized at the transition destination (a route R-13) and a case in which the state point is not stabilized at the transition destination (a route R-23) are assumed.

In the case in which the state point is stabilized at the transition destination (the route R-13) and the case in which the state point is not stabilized at the transition destination (the route R-23), the stability of the state point differs after the transition. In this case, it is sufficient if the output control unit 313 controls output of output information corresponding to the stability of each state point. An example of specific output information will be described later.

Note that in a case in which the user feels his or her internal state meaningful to the user (for example, a state point on which the user concentrates) or a state change (for example, the user can be relaxed quickly), feeling his or her internal state, the user may input a flag associating manipulation. In this case, when the manipulation unit 320 receives the flag associating manipulation from the user, the processing unit 312 may associate the flag with a current state point or a change in a state point. Then, the current state point (and the cluster to which the current state point belongs) can be designated later as a state point of the transition source or the transition destination.

When the user perceives such output information, the user further stabilizes the internal state by the principle of the biofeedback. In addition, the user can learn to further stabilize the internal state. An example of specific output information will be described later.

As described in the foregoing example, output information in accordance with a change in the state point in the physiological index space corresponding to the physiological index value is output. Here, the output information may be visual information (a moving image or a still image), may include sound information, or may be tactile information. Here, a case in which the output information includes a moving image will be described as an example. However, the present disclosure is not limited to a case in which the output information includes a moving image.

Figure 17:
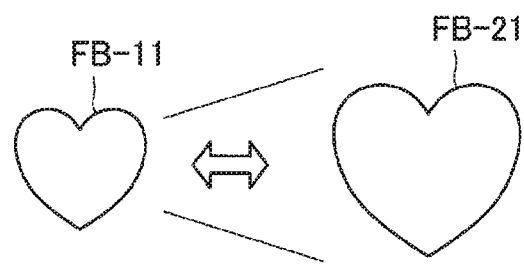
FIG. 17 is a diagram illustrating a display example of output information in accordance with of a distribution density of previous state points for which a current state point serves as a standard.

FIG. 17 is a diagram illustrating a display example of output information in accordance with of a distribution density of previous state points for which a current state point serves as a standard. Referring to FIG. 17, a display object FB-11 and a display object FB-21 are illustrated. The display object FB-11 is a heart type of small object and the display object FB-21 is a heart type of large object. However, the shape and the size of each of the display object FB-11 and the display object FB-21 are not particularly limited.

For example, the output control unit 313 may decide the size of the heart type of object using a value between the display objects FB-11 and FB-21 in accordance with the distribution density of the previous state points for which a state point of the transition destination (a current state point) serves as a standard and may output the size of the object. Specifically, in an example of the foregoing mental stretch training, in a case in which the display object FB-11 in the case of the distribution density of 0 and the display object FB-21 in the case of the distribution density of a maximum value in a space has an intermediate value, an object with an intermediate size between the display objects FB-11 and FB-21 is output in accordance with the intermediate value.

Note that, herein, the case in which the size of the object is decided with a continuous value has been described, but display may be controlled using one threshold or a plurality of thresholds. That is, objects set in two phases or multiple phases may be selected so that a larger display object is formed as the distribution density of the previous state points for which a state point of the transition destination (a current state point) serves as a standard is smaller.

Figure 18:
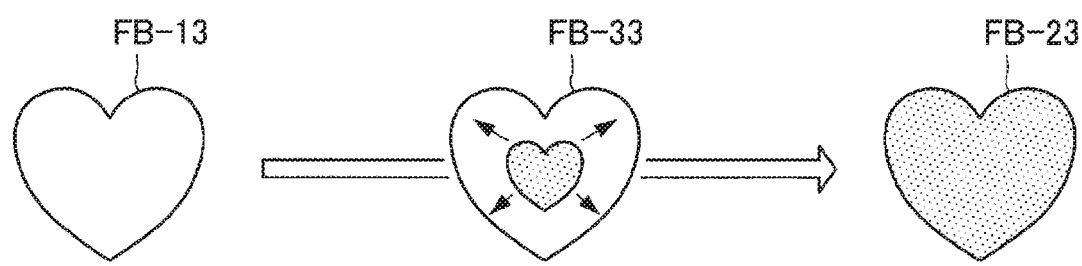
FIG. 18 is a diagram illustrating a display example of the output information in accordance with transition speeds of state points in the physiological index space.

FIG. 18 is a diagram illustrating a display example of the output information in accordance with transition speeds of state points in the physiological index space. Referring to FIG. 18, a display object FB-13, a display object FB-33, and a display object FB-23 are illustrated. The display object FB-13 is a heart type of object with first color (for example, blue) and the display object FB-23 is a heart type of object with second color (for example, green). However, the shape and the color of each of the display object FB-13 and the display object FB-23 are not particularly limited.

For example, in a case in which the transition speed of the state point in the physiological index space (for example, a transition speed from the concentration state to the relaxed state) is greater than the threshold, the output control unit 313 may control output of the display object FB-33 with an animation. The display object FB-33 with an animation may be an animation in which the display object FB-23 appearing to be small inside the display object FB-13 gradually increase. The degree of progress of transition can be calculated in accordance with the position of the current state point and a positional relation between a transition source cluster and a transition destination cluster, but the size of the small object in the inside may gradually increase in accordance with the degree of progress. Conversely, in a case in which the transition speed of the state point in the physiological index space (for example, a transition speed from the concentration state to the relaxed state) is less than the threshold, the output control unit 313 may not display the display object FB-33 with an animation. In this case, by presenting an object with an intermediate color between the display objects FB-13 and FB-23 in accordance with the foregoing degree of progress of the transition, the transition speed may be output to the user using a change in a tone. By outputting the transition speed, the user can obtain quantitative feedback through a gradation change of the tone in a case in which the transition speed is less than the threshold.

In addition, as another realization method, a method of associating the transition speed with the size of the object and associating the distribution density with the tone may be used.

Note that, herein, the case in which the number of thresholds is 1 has been described, but the number of thresholds may be 2 or more. For example, an animation effect to be used may be changed stage by stage in accordance with an increase in the transition speed of the state point in the physiological index space.

Figure 19:
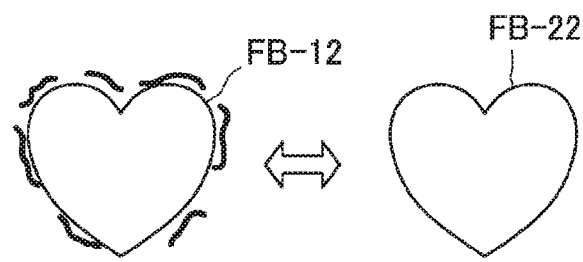
FIG. 19 is a diagram illustrating a display example of output information in accordance with stability of state points in the physiological index space.

FIG. 19 is a diagram illustrating a display example of output information in accordance with stability of state points in the physiological index space. Referring to FIG. 19, the display object FB-12 and the display object FB-22 are illustrated. The display object FB-12 is an object of which a heart type of contour vibrates and the display object FB-22 is an object of which a heart type of contour is still. However, a shape and a motion of each the display object FB-12 and the display object FB-22 are not particularly limited.

For example, the output control unit 313 may control output in accordance with the stability of the state point in the physiological index space. Specifically, the output control unit 313 may perform control such that the display object FB-12 of which the heart type of contour vibrates at a maximum amplitude is output in a case in which the stability of the state point in the physiological index space is less than a predetermined minimum threshold. The output control unit 313 may perform control such that the display object FB-22 of which the heart type of contour is still is output in a case in which the stability of the state point in the physiological index space is greater than a predetermined maximum threshold. The output control unit 313 may perform control such that an object vibrating at an intermediate amplitude is decided between the display objects FB-12 and FB-22 in accordance with a value of the stability and is output in a case in which the stability of the state point in the physiological index space is a value between the predetermined minimum and maximum thresholds.

Note that, herein, the case in which the amplitude is changed in accordance with the stability as the animation effect has been described, but other various effects can also be applied. That is, an animation effect in which a vibration period of the display object is larger as the stability of the state point in the physiological index space is higher may be applied. An animation effect in which the amplitude of the vibration of the display object is smaller as the stability of the state point in the physiological index space is higher may be applied. Both the animation effects may be applied.

As described above, by allocating a predetermined object change to each of the changes in a plurality of state values, it is possible to simultaneously output the changes in the plurality of state values to the user. Additionally, characteristics of various objects such as texture, a shape, luminance, and the like of the objects may correspond to the changes in the state values. Of course, the kinds of changes in the state values may correspond to the kinds of changes in the objects in any way and the present disclosure is not limited thereto.

Figure 20:
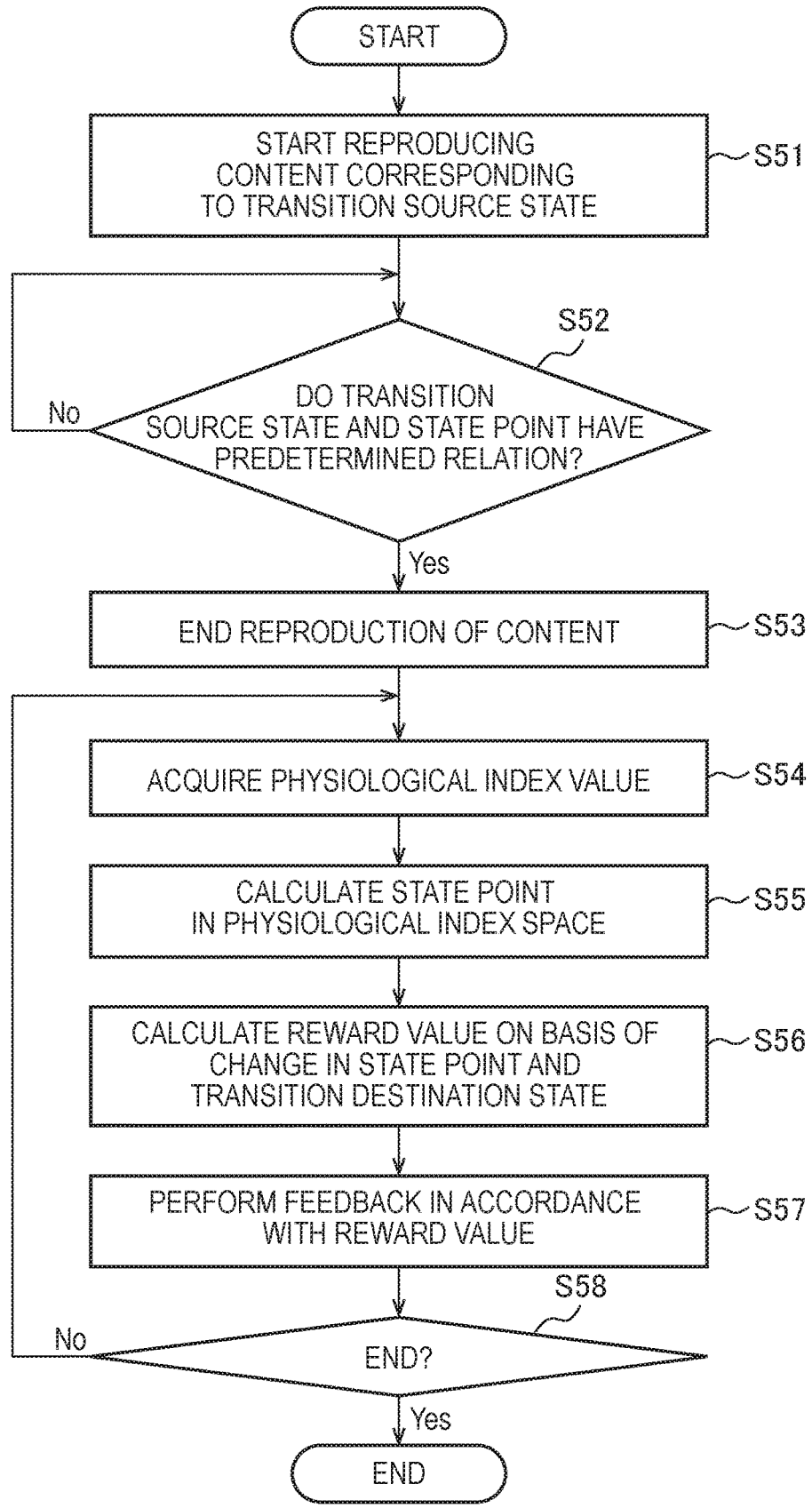
FIG. 20 is an explanatory diagram illustrating a case in which an estimator is generated using a small number of labels and peripheral data.

FIG. 20 is a flowchart illustrating an example of an operation of mental switch training. Note that the flowchart illustrated in FIG. 20 is merely an example of an operation of the mental switch training. Accordingly, the operation of the mental stretch training is not limited to the example of the operation of the flowchart illustrated in FIG. 20.

First, in a case in which the user experiences his or her internal state desired to be designated as the transition source state, the user input a predetermined transition source designation manipulation. The predetermined transition source designation manipulation may be any manipulation (for example, a button pushing manipulation may be used). In a case in which the predetermined transition source designation manipulation by the user is detected, the processing unit 312 associates a flag indicating the transition source state with a state point corresponding to a physiological index value detected at a timing in accordance with detection of the transition source designation manipulation.

In addition, in a case in which the user experiences his or her internal state desired to be designated as the transition destination state, the user input a predetermined transition destination designation manipulation. The predetermined transition destination designation manipulation may be any manipulation (for example, a button pushing manipulation may be used). In a case in which the predetermined transition destination designation manipulation by the user is detected, the processing unit 312 associates a flag indicating the transition destination state with a state point corresponding to a physiological index value detected at a timing in accordance with detection of the transition destination designation manipulation.

At this time, as described above, a case in which the state point associated with the flag indicating the transition source state and the state point associated with the flag indicating the transition destination state are closer than a predetermined distance is assumed. In this case, it is sufficient if the processing unit 312 switches the state point associated with the flag indicating the transition destination state. More specifically, it is sufficient if the processing unit 312 switches the state point associated with the flag indicating the transition destination state to a farthest state point in the cluster corresponding to the state point associated with the flag indicating the transition source state.

Subsequently, as illustrated in FIG. 20, when the generation unit 112 in the information processing device 10 starts reproducing content corresponding to the transition source state (S51), the display unit 260 in the display device 20 outputs the content corresponding to the transition source state. When the user views the content output in this way, the transition source state is aroused. Then, while the user views the content, the sensor unit 330 in the output control device 30 detects the physiological index value.

When the data acquisition unit 311 in the output control device 30 acquires the physiological index value, the processing unit 312 calculates the state point in the physiological index space corresponding to the physiological index value. The output control unit 313 controls output indicating that the current state reaches the transition source state in a case in which the state point associated with the flag indicating the transition source state and the current state point satisfy a predetermined relation (for example, a case in which the state points belong to the same cluster, or the like) ("Yes" in S52). The generation unit 112 ends the reproduction of the content corresponding to the transition source state (S53). Conversely, the output control unit 313 returns the process to S52 in a case in which the state point associated with the flag indicating the transition source state and the current state point do not satisfy the predetermined relation ("No" in S52).

When the data acquisition unit 311 in the output control device 30 acquires the physiological index value (S54), the processing unit 312 calculates the state point in the physiological index space corresponding to the physiological index value (S55). The processing unit 312 calculates displacement from an initial (transition source) state point to the current state point as the change in the state point and calculates the reward value on the basis of a positional relation with the state point of the transition destination (S56). Here, as the change in the state point, the distribution density of the previous state points for which the current state point serves as a standard, the transition speed of the state point, the stability of the state point, and the like may be additionally calculated and reflected in the reward value. Then, the output control unit 313 performs feedback in accordance with the reward value (output control of the output information in accordance with the reward value) (S57).

Here, the reward value may be calculated on the basis of the change in the state point and the transition destination state in any way. The output control unit 313 may perform feedback in accordance with the reward value. For example, the feedback may be performed in accordance with the transition speed illustrated in FIG. 18 using information regarding the foregoing initial (transition source) state point, the current state point, and the state point of the transition destination. Alternatively, while the feedback in accordance with the reward value is repeated, the output control unit 313 may control output indicating that the current internal state reaches the transition destination state in a case in which the state point associated with the flag indicating the transition destination state and the current state point satisfy a predetermined relation.

In a case in which the mental switch training continues ("No" in S58), the control unit 310 returns the process to S54. Conversely, in a case in which the mental switch training ends ("Yes" in S58), the control unit 310 ends the operation. The calculation of the reward value based on the change in the state point and the feedback in accordance with the reward value have been described above.

Through the mental switch training, the following effects can be obtained. First, the user can train switching between the internal states in which training is difficult until now through the mental switch training. For example, the user can train switching between two internal states that have a short distance in the physiological index space. In addition, the user can train direct switching without passing through a distant internal state once, in addition, it is possible to train an improvement in the transition speed of the internal state.

In addition, through the mental switch training, it is possible to obtain the advantageous effect of separating a distance in the physiological index space corresponding to two internal states. Thus, it is easy for the user to transition between the two internal states as a psychological state using a change in the physiological state as an opportunity. For example, since it is easy for the user to detect a difference between the physiological states of the tension and the concentration, it is easy to switch the psychological state to the concentration state using perception of the change in the physiological state as an opportunity. In addition, since a distance between the clusters of the tension and the concentration extends, an influence of fluctuation of a state value is rarely received and it is easier to maintain the concentrated state.

In addition, by drifting a direction of the change in a more preferable direction in a target internal state, it is possible to obtain a preferred internal state. For example, when concentration is deepened in a previous internal state, only the degree of sympathetic nerve activity may increase unilaterally and over-tension may easily arise. In this case, by drifting a transition destination state value in a direction in which the degree of parasympathetic nerve activity is high, it is possible to maintain the deep concentration state more stably. In general, a suitable internal state point differs depending on an individual and differs depending on an environment or a situation even for the same individual. However, through the individualization learning, it is possible to search for a transition destination point appropriate for the user.

In addition, through the mental switch training, a difference in an internal state actually appearing in the user can be used as a starting point for training. In addition, by widening the difference in the internal state actually appearing in the user, it is possible to guide the internal state of the user to a preferred internal state.

The mental switch training has been mainly described above.

3. OVERVIEW OF GENERATION OF ESTIMATOR

It is possible to estimate an internal state of the user on the basis of a physiological index value detected by the biosensor. As an estimator estimating an internal state of the user, an estimator to be described below can also be used. Hereinafter, an overview of generation of an estimator estimating an internal state of the user will be described. First, a case in which an internal state of the user is estimated using peripheral data detected with a wearable device will be assumed.

Figure 21:
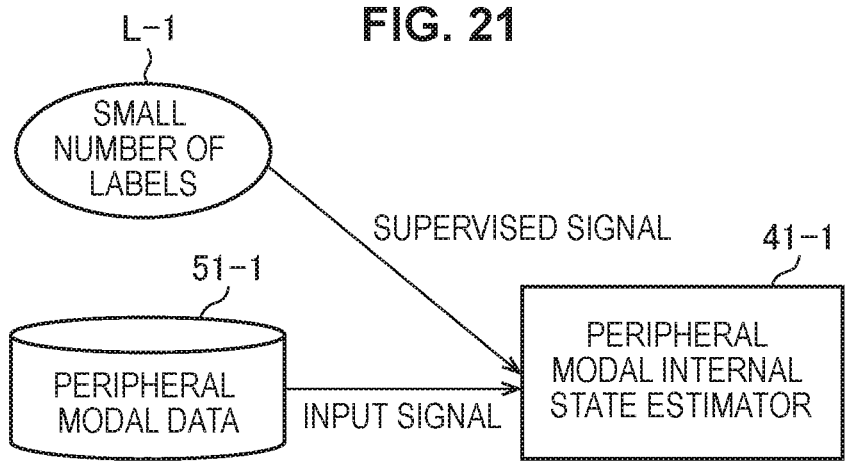
FIG. 21 is an explanatory diagram illustrating a case in which an estimator is generated using a small number of labels and peripheral data.

FIG. 21 is an explanatory diagram illustrating a case in which an estimator is generated using a small number of labels and peripheral data. Referring to FIG. 21, a case in which a peripheral modal internal state estimator 41-1 is generated through machine learning using a small number of labels L-1 as a supervised signal and using peripheral modal data (peripheral data) 51-1 as an input signal is illustrated. However, in a case in which an internal state of the user is estimated using the peripheral data, the peripheral data is detected in a location distant from the center in which most of the internal states are decided. Therefore, an amount of information regarding the internal states is less than the central data and it is difficult to estimate an internal state with high precision.

Figure 22:
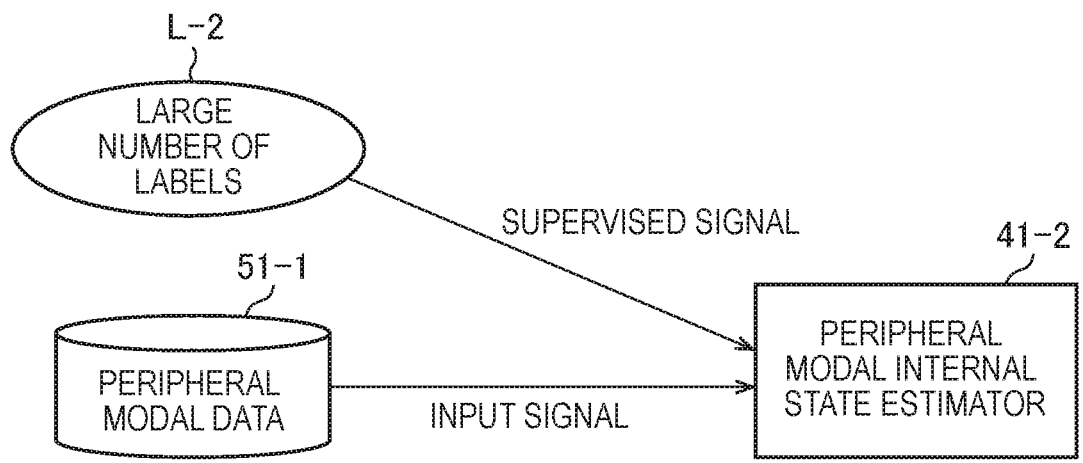
FIG. 22 is an explanatory diagram illustrating a case in which an estimator is generated using a large number of labels and peripheral data.

Here, to improve the precision of the estimation of the internal state, a case in which a large number of labels is manually produced will be assumed. FIG. 22 is an explanatory diagram illustrating a case in which an estimator is generated using a large number of labels and peripheral data. Referring to FIG. 22, a case in which the peripheral modal internal state estimator 41-1 is generated through machine learning using a large number of labels L-2 as a supervised signal and using the peripheral modal data (peripheral data) 51-1 as an input signal is illustrated.

However, to manually produce a large number of labels, cost increases. In addition, work for producing the labels may affect a psychological state of the user (a concentration state, a relaxed state, or the like may be distracted). In addition, since people are not necessarily always conscious of a concentration state and a relaxed state, it is difficult to continuously acquire appropriate labels.

Figure 23:
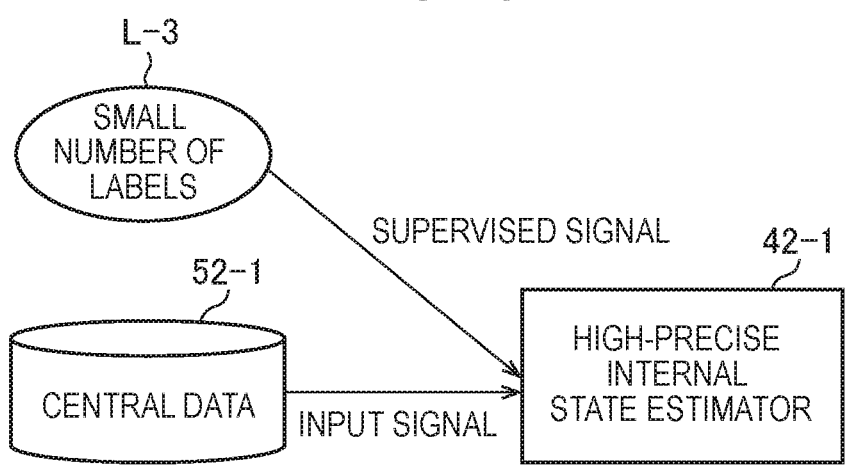
FIG. 23 is an explanatory diagram illustrating a case in which an estimator is generated using a small number of labels and central data.

On the other hand, a case in which an internal state of the user is estimated using central data such as brain waves will be assumed. FIG. 23 is an explanatory diagram illustrating a case in which an estimator is generated using a small number of labels and central data. Referring to FIG. 23, a case in which a high-precise internal state estimator 42-1 is generated through machine learning using a small number of labels L-3 as a supervised signal and using central data 52-1 as an input signal is illustrated.

One kind of label value may be added to the central data 52-1 in an entire section of a certain time, but sections of a plurality of times with a plurality of different label values may be included. In this case, one of two or more kinds of labels may be added to each of the sections of the plurality of times included in the central data 52-1. In addition, the added labels may be continuous values.

Figure 24:
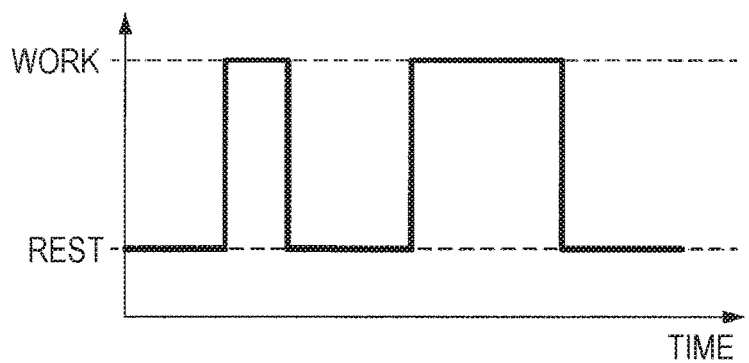
FIG. 24 is a diagram illustrating an example in which two kinds of labels are added to a plurality of sections included in the central data.

FIG. 24 is a diagram illustrating an example in which two kinds of labels are added to sections of a plurality of times included in the central data 52-1. As illustrated in FIG. 24, two kinds of labels may be values indicating that work is in progress or values indicating that a rest is in progress. For example, the work may be work for playing game content, or the like. Alternatively, two kinds of labels may be a value indicating an internal state (a value indicating the concentration state or not).

Figure 25:
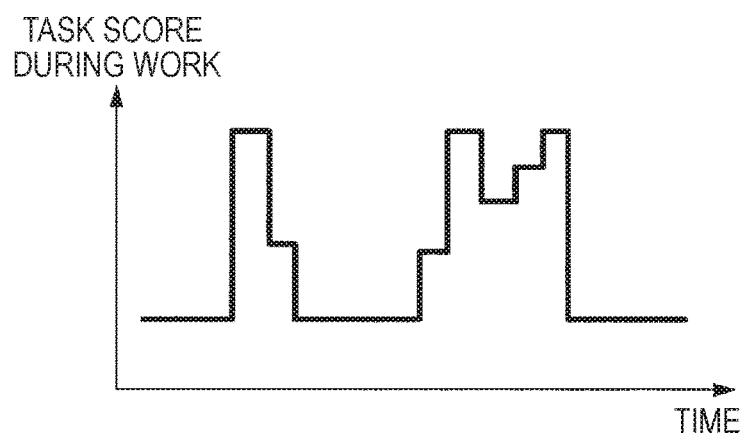
FIG. 25 is a diagram illustrating an example in which three or more kinds of labels are added to a plurality of sections included in the central data.

FIG. 25 is a diagram illustrating an example in which three or more kinds of labels are added to sections of a plurality of times included in the central data 52-1. As illustrated in FIG. 25, three or more kinds of labels may be continuous values such as task scores during work. For example, the task scores during work may be scores of game content in a case in which the work is work for playing the game content. Alternatively, the three or more kinds of labels may be values indicating internal states (a concentration state, a cautious state, a sleeping state, and a relaxed state, and the like). At this time, one of these internal states may be estimated using a peripheral modal internal state estimator 41-3.

In this way, the internal state of the user can be estimated using the central data. However, in a current device technology, daily estimation of the central data may burden the user. In addition, since the central data is sensitive data, it is important to remove noise from the central data, but it is difficult to sufficiently exclude the noise.

Accordingly, it is important to estimate the internal state of the user more robustly and with higher precision in various occasions. Accordingly, hereinafter, a technology for estimating an internal state of the user more robustly and with higher precision will be mainly described.

4. EMBODIMENT OF GENERATION OF ESTIMATOR

Figure 26:
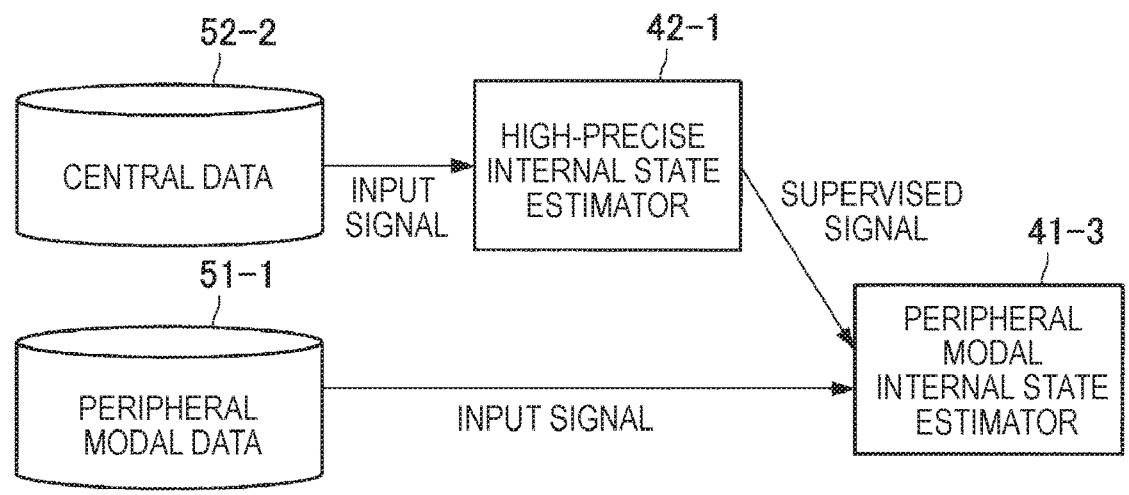
FIG. 26 is an explanatory diagram illustrating an example of generation of an estimator according to the embodiment.

FIG. 26 is an explanatory diagram illustrating an example of generation of an estimator according to the embodiment. First, as described with reference to FIG. 23, the generation unit 112 generates the high-precise internal state estimator 42-1 (a first state estimator) on the basis of central data 52-2 (first central data) and a label (for example, the small number of labels L-3) associated with the central data 52-2. More specifically, the generation unit 112 generates the high-precise internal state estimator 42-1 using the label as a first supervised signal and using the central data 52-2 as a first input signal through the machine learning. The acquisition unit 111 acquires the high-precise internal state estimator 42-1 generated in this way.

In addition, as illustrated in FIG. 26, the generation unit 112 generates the peripheral modal internal state estimator 41-3 (a second state estimator) on the basis of the peripheral modal data 51-1 (peripheral data) and the internal state of the user estimated on the basis of the central data 52-2 (second central data) and the high-precise internal state estimator 42-1. More specifically, the generation unit 112 generates the peripheral modal internal state estimator 41-3 using the estimated internal state of the user as the second supervised signal and using the peripheral modal data 51-1 as second input signal through the machine learning. The central data 52-2 and the peripheral modal data 51-1 are detected at corresponding timings (for example, substantially the same timing).

As described above, in the embodiment of the present disclosure, the estimation is performed using peripheral data instead of central data which burdens measurement in a daily environment. In addition, to estimate an internal state with high precision from the peripheral data, a large number of state points and supervised labels are necessary. However, outputs of the estimator by the central data obtained with a small number of labels through the machine learning is used as labels instead of using a large number of labels which time and effort are required to manually generate. In this way, according to the embodiment of the present disclosure, the high-precise peripheral modal internal state estimator 41-3 can be generated using the central data (for example, a large amount of central data) and the robust peripheral modal data.

The advantages that the estimator of the peripheral data is learned using the central data are as follows. First, labels of many samples can be generated for a long time and can be learned inexpensively. For example, it is possible to generate labels reflecting internal states more directly than labels decided subjectively. In addition, acquisition of the labels does not distract the internal states. That is, evaluation behaviors of the internal states do not affect psychological states. In addition, since physiological signals are directly measured, labels can be continuously generated.

The advantages that the peripheral data reflecting autonomic nerve activity is used are as follows. First, in autonomic nerve activity, a time constant of reaction is in the range of several seconds to several minutes. Therefore, an estimator using peripheral data performs more stable estimation output than an estimator using central data rapidly changing in units of milliseconds. In addition, since autonomic nerve activity is activity related to relaxing, concentration, or the like, the autonomic nerve activity is appropriate for estimating current performance of people.

In addition, in the label association work, the user is allowed to view content to which a label is added. That is, it is sufficient if the generation unit 112 associates a label with the central data 52-2 detected while the content is output. Thus, the machine learning is expected to be performed more appropriately. Further, the content may include VR content configured using VR. Then, since the user can enjoy the feeling of presence more strongly, an internal state of the user is expected to be aroused more strongly.

In addition, the precision of the peripheral modal internal state estimator 41-3 can change in accordance with a learning stage. Accordingly, the user may be allowed to ascertain how much the precision of the peripheral modal internal state estimator 41-3 is improved. Accordingly, in a case in which a relation between an output of the high-precise internal state estimator 42-1 based on the central data and an estimation result based on the peripheral data by the peripheral modal internal state estimator 41-3 satisfies a predetermined condition, the output unit 113 may output predetermined output information (for example, information or the like indicating an improvement in the precision of the estimator).

For example, the predetermined output information may be subjected to output control by the output control unit 313 in the output control device 30 to be perceived by the user. For example, the predetermined condition may include a condition that an error between the estimation result by the peripheral modal internal state estimator 41-3 and the output of the high-precise internal state estimator 42-1 based on the central data is less than a threshold. In addition, the precision of the peripheral modal internal state estimator 41-3 may be reflected in content. For example, game content which does not progress earlier until generation of the peripheral modal internal state estimator 41-3 of which the precision exceeds the threshold may be supplied.

In addition, in a case in which the precision of the peripheral modal internal state estimator 41-3 is sufficiently high, the foregoing various outputs can be supplied to the user using only the output control device 30. In a case in which such an operation is performed, the display device 20 and the information processing device 10 are not necessary. Even in an environment in which many devices may not be disposed, such as outdoor or office environments, the user can perform measurement of peripheral data using only the output control device 30 which is a wearable device and can enjoy desired outputs.

Figure 27:
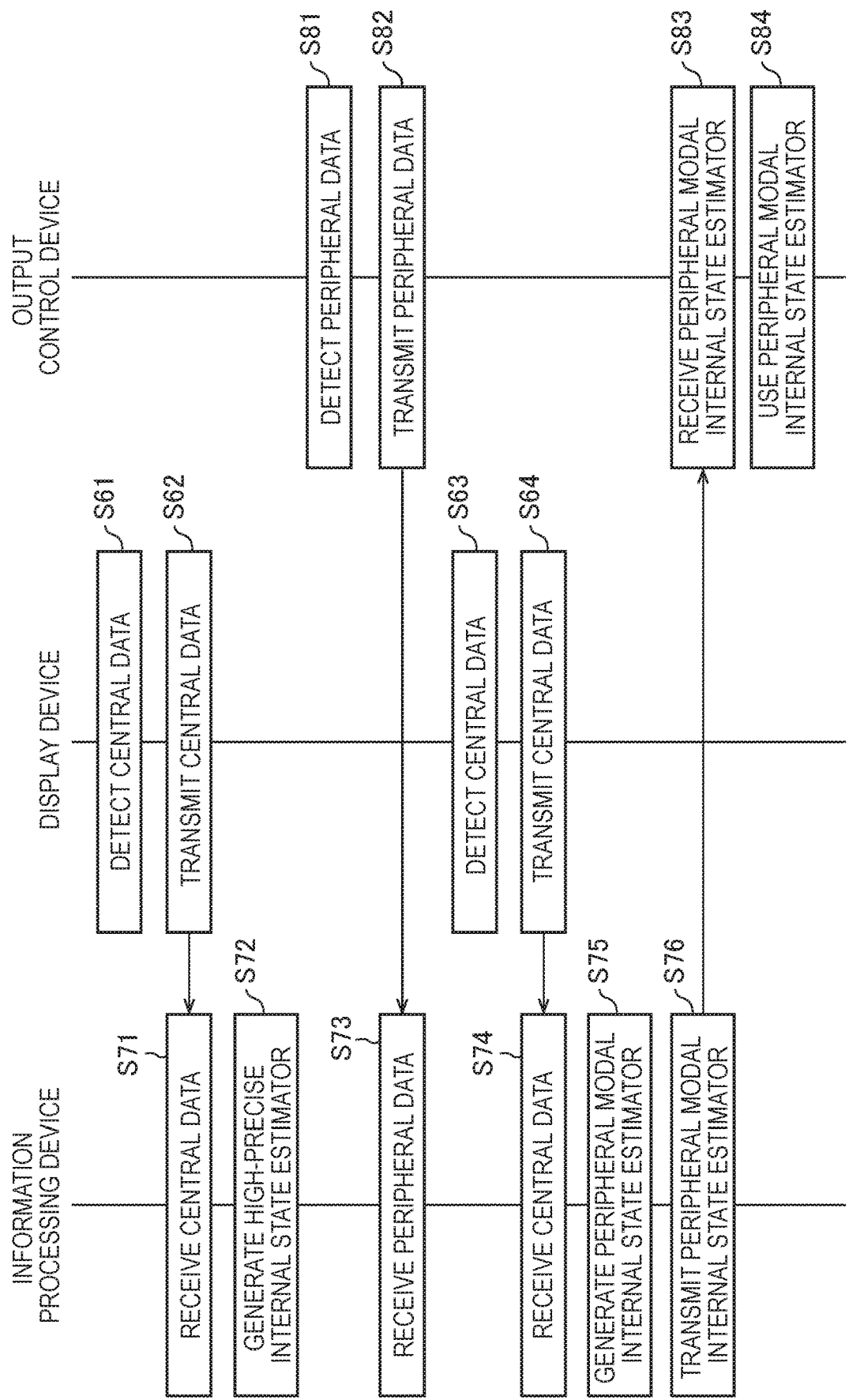
FIG. 27 is a flowchart illustrating an example of a generation operation by the estimator according to the embodiment.

FIG. 27 is a flowchart illustrating an example of a generation operation by the estimator according to the embodiment. As illustrated in FIG. 27, the display device 20 detects central data and transmits the central data to the information processing device 10 (S62). The information processing device 10 receives the central data (S71). Then, the information processing device 10 generates a high-precise internal state estimator on the basis of the central data and the label (S72).

In addition, the output control device 30 detects peripheral data (S81) and transmits the peripheral data to the information processing device 10 (S82). The information processing device 10 receives the peripheral data (S73). Further, the display device 20 detects central data at a timing corresponding to the detection of the peripheral data (S63) and transmits the central data to the information processing device 10 (S64). The information processing device 10 receives the central data (S74). Then, the information processing device 10 generates a peripheral modal internal state estimator on the basis of the high-precision internal state estimator, the central data, and the peripheral data (S75).

The information processing device 10 transmits the peripheral modal internal state estimator to the output control device 30 (S76) and the output control device 30 receives the peripheral modal internal state estimator (S83). The output control device 30 performs internal state estimation of the user using the peripheral modal internal state estimator (S84).

In the generation of the estimators according to the embodiment, it is possible to acquire brain waves and peripheral data during work of the user (for example, desk work) for a long time. Then, the estimators can be generated using the labels and the peripheral data generated using the brain waves. As a result, it is possible to determine a task relaxing state with sufficiently high precision. The user shows a response in a stage in accordance with work load. Since the peripheral data is not sensitive like brain waves, an estimation result obtained using the peripheral data indicates a stable result even at a general desk work time.

For example, estimators using average peripheral data obtained by measuring many people in advance can be prepared in advance and the estimators can also be utilized. In this case, once the user wears a brain wave meter, internal state estimation precision of the user is considered to increase.

5. HARDWARE CONFIGURATION EXAMPLE

Figure 28:
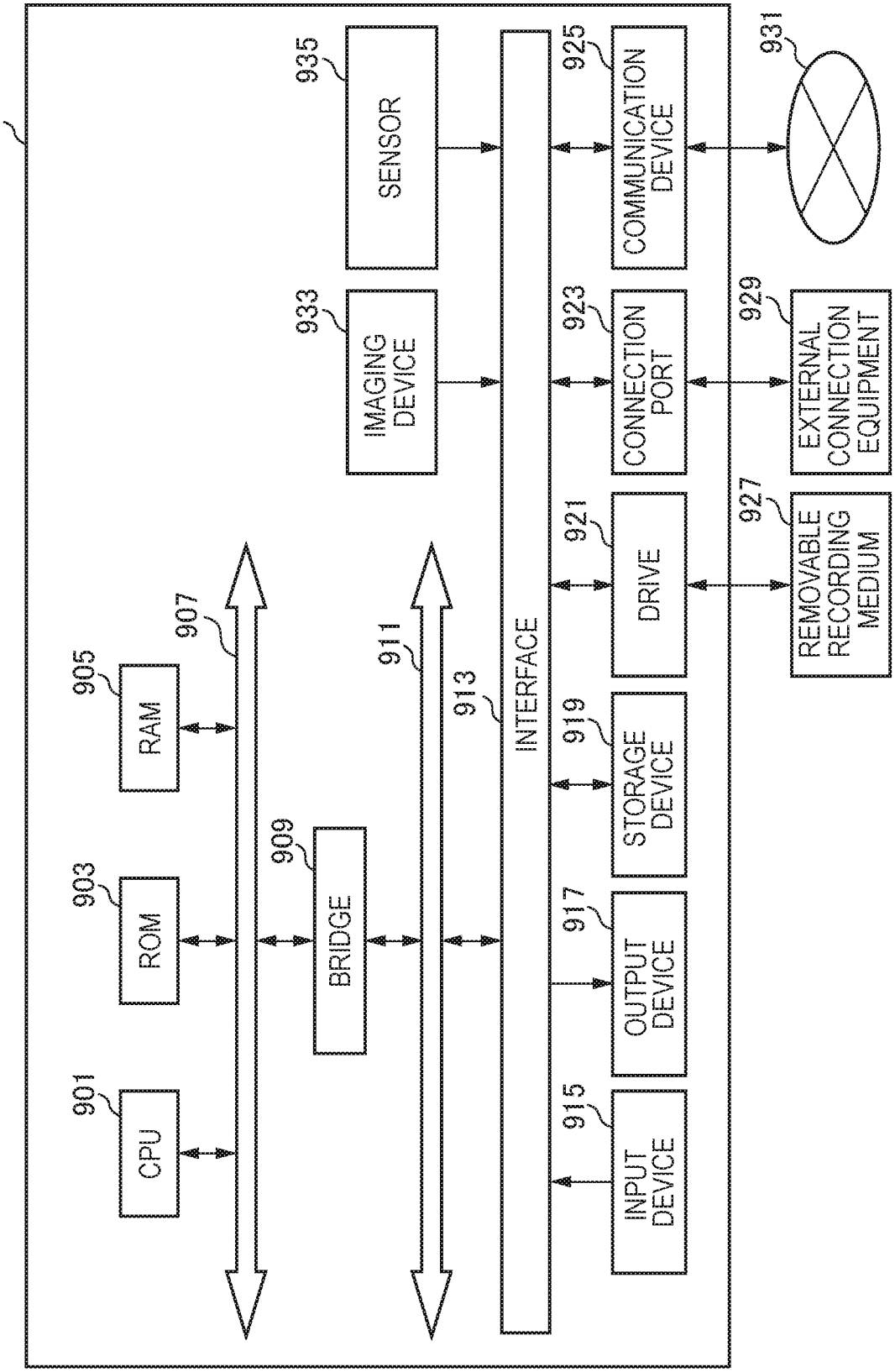
FIG. 28 is a block diagram illustrating a hardware configuration example of the information processing device according to the embodiment.

Next, with reference to FIG. 28, a hardware configuration of the information processing device 10 according to the embodiment of the present disclosure will be described. FIG. 28 is a block diagram illustrating the hardware configuration example of the information processing device 10 according to the embodiment of the present disclosure. Note that hardware configurations of the display device 20 and the output control device 30 according to the embodiment of the present disclosure can also be realized as in the hardware configuration example of the information processing device 10 illustrated in FIG. 28.

As illustrated in FIG. 28, the information processing device 10 includes a central processing unit (CPU) 901, read only memory (ROM) 903, and random access memory (RAM) 905. The control unit 110 can be realized by the CPU 901, the ROM 903, and the RAM 905. In addition, the information processing device 10 may include a host bus 907, a bridge 909, an external bus 911, an interface 913, an input device 915, an output device 917, a storage device 919, a drive 921, a connection port 923, and a communication device 925. Moreover, the information processing device 10 may include an imaging device 933 and a sensor 935, as necessary. The information processing device 10 may include a processing circuit such as a digital signal processor (DSP) or an application specific integrated circuit (ASIC), alternatively or in addition to the CPU 901.

The CPU 901 serves as an arithmetic processing device and a control device, and controls the overall operation or a part of the operation of the information processing device 10 according to various programs recorded in the ROM 903, the RAM 905, the storage device 919, or a removable recording medium 927. The ROM 903 stores programs, operation parameters, and the like used by the CPU 901. The RAM 905 temporarily stores programs used when the CPU 901 is executed, and parameters that change as appropriate when executing such programs. The CPU 901, the ROM 903, and the RAM 905 are connected with each other via the host bus 907 configured from an internal bus such as a CPU bus. In addition, the host bus 907 is connected to the external bus 911 such as a Peripheral Component Interconnect/Interface (PCI) bus via the bridge 909.

The input device 915 is a device operated by a user such as a button. The input device 915 may include a mouse, a keyboard, a touchscreen, a switch, and a lever. In addition, the input device 915 may include a microphone configured to detect voice of users. The input device 915 may be a remote control device that uses, for example, infrared radiation and another type of radio waves. Alternatively, the input device 915 may be external connection equipment 929 such as a mobile phone that corresponds to an operation of the information processing device 10. The input device 915 includes an input control circuit that generates input signals on the basis of information which is input by a user to output the generated input signals to the CPU 901. A user inputs various types of data and indicates a processing operation to the information processing device 10 by operating the input device 915. In addition, the imaging device 933 (to be described later) may function as the input device by capturing an image of movement of hands of a user or capturing a finger of a user. In this case, a pointing position may be decided in accordance with the movement of the hands or a direction of the finger. Note that the manipulation unit 120 described above can be realized by input device 915.

The output device 917 includes a device that can visually or audibly report acquired information to a user. The output device 917 may be, for example, a display device such as a liquid crystal display (LCD), or an organic electro-luminescence (EL) display, a sound output device such as a speaker or a headphone. Further, the output device 917 may include, for example, a plasma display panel (PDP), a projector, a hologram display device, or a printer. The output device 917 outputs a result obtained through a process performed by the information processing device 10, in the form of text or video such as an image, or sounds such as voice and audio sounds. In addition, the output device 917 may include a light or the like to light the surroundings.

The storage device 919 is a device for data storage that is an example of the storage unit of the information processing device 10. The storage device 919 includes, for example, a magnetic storage device such as a hard disk drive (HDD), a semiconductor storage device, an optical storage device, or a magneto-optical storage device. The storage device 919 stores therein various data and programs executed by the CPU 901, and various data acquired from an outside.

The drive 921 is a reader/writer for the removable recording medium 927 such as a magnetic disk, an optical disc, a magneto-optical disk, and a semiconductor memory, and built in or externally attached to the information processing device 10. The drive 921 reads out information recorded on the mounted removable recording medium 927, and outputs the information to the RAM 905. The drive 921 writes the record into the mounted removable recording medium 927.

The connection port 923 is a port used to directly connect equipment to the information processing device 10. The connection port 923 may be a USB (Universal Serial Bus) port, an IEEE1394 port, and a Small Computer System Interface (SCSI) port, or the like. In addition, the connection port 923 may be an RS-232C port, an optical audio terminal, an HDMI (registered trademark) (High-Definition Multimedia Interface) port, and so on. The connection of the external connection equipment 929 to the connection port 923 makes it possible to exchange various kinds of data between the information processing device 10 and the external connection equipment 929.

The communication device 925 is a communication interface including, for example, a communication device for connection to the network 931. The communication device 925 may be, for example, a wired or wireless local area network (LAN), Bluetooth (registered trademark), or a communication card for a wireless USB (WUSB). The communication device 925 may also be, for example, a router for optical communication, a router for asymmetric digital subscriber line (ADSL), or a modem for various types of communication. For example, the communication device 925 transmits and receives signals in the Internet or transmits signals to and receives signals from another communication device by using a predetermined protocol such as TCP/IP. The network 931 to which the communication device 925 connects is a network established through wired or wireless connection. The network 931 is, for example, the Internet, a home LAN, infrared communication, radio communication, or satellite communication. Note that the communication unit 150 described above can be realized by the communication device 925.

The imaging device 933 is a device that captures images of a real space by using an image sensor such as a charge coupled device (CCD) or a complementary metal oxide semiconductor (CMOS), and various members such as a lens for controlling image formation of a subject image onto the image sensor, and generates the captured images. The imaging device 933 may capture a still image or a moving image. Note that the foregoing sensor unit 130 can be realized by the imaging device 933. The imaging device 933 may be installed inside a goggle in the display device 20 to detect biometric information such as a visual line direction, a pupil diameter, blink, and an open status of an eyelid.

The sensor 935 is various sensors such as a ranging sensor, an acceleration sensor, a gyro sensor, a geomagnetic sensor, a vibration sensor, an optical sensor, and a sound sensor. The sensor 935 acquires information regarding a state of the information processing device 10 such as a posture of a housing of the information processing device 10, and information regarding an environment surrounding the information processing device IC) such as luminous intensity and noise around the information processing device 10. The sensor 935 may include a global positioning system (GPS) sensor that receives GPS signals to measure latitude, longitude, and altitude of the device. Note that the foregoing detection unit 130 can be realized by the sensor 935. The sensor 935 also includes, for example, various biosensors such as a brain wave sensor, a magnetoencephalographic sensor, an NIRS sensor, a pulse sensor, an electro-oculogram sensor, a bloodstream sensor, an SPO2 sensor, a perspiration sensor, and a temperature sensor to acquire biometric information in the display device 20. In addition, the sensor 935 also includes, for example, various biometric sensors such as a pulse sensor, a myoelectric sensor, a bloodstream sensor, an SPO2 sensor, a perspiration sensor, and a temperature sensor to acquire peripheral information in the output control device 30.

6. CONCLUSION

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, when operations of the foregoing information processing device 10, display device 20, and output control device 30 are realized, the position of each configuration is not particularly limited. Some of the processes of the units in the information processing device 10 may be performed by the display device 20 or the output control device 30. In addition, some of the processes of the units in the display device 20 and the output control device 30 may be performed by the information processing device 10.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An output control device including:
an output control unit configured to control output of output information in accordance with a change in a state point in a physiological index space corresponding to a physiological index value based on a biosensor.

(2)

The output control device according to (1), in which the output control unit controls the output of the output information in accordance with distribution density of previous state points for which a current state point serves as a standard in the physiological index space.

(3)

The output control device according to (1) or (2), in which the output control unit controls the output of the output information in accordance with a transition speed of the state point in a physiological index space.

(4)

The output control device according to any one of (1) to (3), in which the output control unit controls the output of the output information in accordance with stability of the state point in the physiological index space.

(5)

The output control device according to any one of (1) to (4), in which the output control unit acquires a reward value in accordance with the change in the state point in the physiological index space and controls the output of the output information in accordance with the reward value.

(6)

The output control device according to any one of (1) to (5), in which the physiological index value is detected by the biosensor while content is output.

(7)

The output control device according to any one of (1) to (6), including:
a processing unit configured to associate a flag indicating a transition source state with the state point corresponding to the physiological index value detected by the biosensor at a timing in accordance with detection of a predetermined transition source designation manipulation in a case in which the transition source designation manipulation by a user is detected.

(8)

The output control device according to (7), in which the output control unit controls output indicating that a current internal state reaches the transition source state in a case in which the state point associated with the flag indicating the transition source state and the current state point satisfy a predetermined relation.

(9)

The output control device according to any one of (1) to (6), including:
a processing unit configured to associate a flag indicating a transition destination state with the state point corresponding to the physiological index value detected by the biosensor at a timing in accordance with detection of a predetermined transition destination manipulation in a case in which the transition destination manipulation b a user is detected.

(10)

The output control device according to (9), in which the output control unit controls output indicating that the current internal state reaches the transition destination state in a case in which the state point associated with the flag indicating the transition destination state and the current state point satisfy a predetermined relation.

(11)

The output control device according to (9) or (10), in which the processing unit switches the state point associated with the flag indicating the transition destination state in a case in which the state point associated with the flag indicating the transition source state and the state point associated with the flag indicating the transition destination state are closer than a predetermined distance.

(12)

The output control device according to any one of (1) to (11), in which the physiological index value includes a physiological index value reflecting autonomic nerve activity.

(13)

The output control device according to (12), in which the biological index value reflecting the autonomic nerve activity includes a physiological index value based on at least one of a perspiration sensor, an electrocardiographic sensor, a pulse sensor, or a peripheral bloodstream sensor.

(14)

The output control device according to any one of (1) to (13), in which the physiological index value includes a physiological index value reflecting central nerve activity.

(15)

The output control device according to (14), in which the physiological index value reflecting the central nerve activity includes a physiological index value based on a brain wave sensor.

(16)

The output control device according to any one of (1) to (15), in which a plurality of state points in the physiological index space are classified into a plurality of clusters by machine learning.

(17)

The output control device according to (16), in which a label added to content output at a timing in accordance with detection of a corresponding physiological index value is associated with each of the plurality of clusters.

(18)

The output control device according to (17), in which the label is corrected on the basis of evaluation information for the content.

(19)

An output control method including: by a processor,
controlling output of output information in accordance with a change in a state point in a physiological index space corresponding to a physiological index value based on a biosensor.

(20)

A program causing a computer to function as an output control device including an output control unit configured to control output of output information in accordance with a change in a state point in a physiological index space corresponding to a physiological index value based on a biosensor.

In addition, the present technology may also be configured as below.

(1)

An information processing device including:
- an acquisition unit configured to acquire a first state estimator generated on the basis of first central data and a label associated with the first central data; and
- a generation unit configured to generate a second state estimator on the basis of peripheral data and a state of a user estimated on the basis of second central data and the first state estimator.

(2)

The information processing device according to (1),
in which the label is added to content, and
the label is associated with the first central data detected while the content is output.

(3)

The information processing device according to (2),
in which the content includes virtual reality (VR) content configured using VR.

(4)

The information processing device according to any one of (1) to (3) including:
- an output unit configured to output predetermined output information in a case in which a relation between output of the first state estimator based on the second central data and an estimation result based on the peripheral data by the second state estimator satisfies a predetermined condition.

(5)

The information processing device according to (4),
in which the predetermined condition includes a condition that an error between the estimation result and output of the first state estimator based on the second central data is less than a threshold.

(6)

The information processing device according to any one of (1) to (5), in which the second central data and the peripheral data are detected at corresponding timings.

(7)

The information processing device according to any one of (1) to (6), in which one of two or more kinds of labels is added to each of sections of a plurality of times included in the first central data.

(8)

The information processing device according to any one of (1) to (7), in which the first state estimator is generated through machine learning using the label as a first supervised signal and using the first central data as a first input signal.

(9)

The information processing device according to any one of (1) to (8), in which the generation unit generates the second state estimator through machine learning using the state of the user as a second supervised signal and using the peripheral data as a second input signal.

(10)

The information processing device according to any one of (1) to (9), in which the generation unit generates the first state estimator on the basis of the first central data and the label.

(11)

The information processing device according to any one of (1) to (10), in which the peripheral data includes a physiological index value reflecting autonomic nerve activity.

(12)

The information processing device according to (11), in which the physiological index value reflecting the autonomic nerve activity includes a physiological index value based on one of a perspiration sensor, an electrocardiographic sensor, a pulse sensor, and a peripheral bloodstream sensor.

(13)

The information processing device according to any one of (1) to (12), in which each of the first central data and the second central data includes a physiological index value reflecting central nerve activity.

(14)

The information processing device according to (13), in which the physiological index value reflecting the central nerve activity includes a physiological index value based on a brain wave sensor.

(15)

An information processing method including: by a processor,
- acquiring a first state estimator generated on the basis of first central data and a label associated with the first central data; and
- generating a second state estimator on the basis of peripheral data and a state of a user estimated on the basis of second central data and the first state estimator.

(16)

A program causing a computer to function as an information processing device including:
- an acquisition unit configured to acquire a first state estimator generated on the basis of first central data and a label associated with the first central data; and
- a generation unit configured to generate a second state estimator on the basis of peripheral data and a state of a user estimated on the basis of second central data and the first state estimator.

REFERENCE SIGNS LIST 1 information processing system
10 information processing device
110 control unit
111 acquisition unit
112 generation unit
113 output unit
120 manipulation unit
130 sensor unit
140 storage unit
150 communication unit
20 display device
210 control unit
220 manipulation unit
230 sensor unit
240 storage unit
250 communication unit
260 display unit
30 output control device
310 control unit
311 data acquisition unit
312 processing unit
313 output control unit
320 manipulation unit 330 sensor unit
340 storage unit
350 communication unit
360 presentation unit

The invention claimed is:
1. An output control device comprising:
a biosensor; and
an output control unit configured to
receive a plurality of physiological index values from the biosensor,
plot the plurality of physiological index values to a state point in a physiological index space,
control display of a display object on a graphical computer display in accordance with a change in the state point in the physiological index space corresponding to the physiological index value,
control the display of the display object on the graphical computer display based on a transition speed of the state point in the physiological index space,
control the display of the display object in accordance with stability of the state point in the physiological index space, and
control an output of the display object displayed on the graphical computer display to be displayed as a graphical animated display object based on the transition speed being greater than a predetermined threshold, and
wherein the graphical animated display object is an animation in which an amplitude or a period of vibration of the display object displayed on the graphical computer display changes according to the stability of the state point in the physiological index space,
wherein the graphical animated display object is an animation in which a size of the display object changes according to a degree of progress of transition,
wherein the degree of progress of transition is calculated in accordance with a position of a current state point in the physiological index space and a positional relation between a transition source cluster and a transition destination cluster, and
wherein the output control unit is implemented via at least one processor.

2. The output control device according to claim 1, wherein the output control unit is further configured to
control the display of the display object based on distribution density of previous state points in the physiological index space at a position of the current state point in the physiological index space.

3. The output control device according to claim 2, wherein the output control unit is further configured to
control the size of the display object displayed on the graphical computer display to be a first size based on the distribution density of the previous state points in the physiological index space at the position of the current state point in the physiological index space being a first density, and
control the size of the display object displayed on the graphical computer display to be a second size larger than the first size based on the distribution density of the previous state points in the physiological index space at the position of the current state point in the physiological index space being a second density larger than the first density.

4. The output control device according to claim 2, wherein the output control unit is further configured to control the size of the display object displayed on the graphical computer display to have a direct relationship with the distribution density of the previous state points at the position of the current state point in the physiological index space.

5. The output control device according to claim 1, wherein the output control unit is further configured to
acquire a reward value in accordance with the change in the state point in the physiological index space, and
control the display of the display object in accordance with the reward value.

6. The output control device according to claim 1, wherein the physiological index value is detected by the biosensor while content is output.

7. The output control device according to claim 1, further comprising:
a processing unit configured to associate a flag indicating a transition source state with the state point corresponding to the physiological index value detected by the biosensor at a timing in accordance with detection of a predetermined transition source designation manipulation in a case in which the predetermined transition source designation manipulation by a user is detected,
wherein the processing unit is implemented via at least one processor.

8. The output control device according to claim 7, wherein the output control unit is further configured to control output indicating that a current internal state reaches the transition source state in a case in which the state point associated with the flag indicating the transition source state and the current state point satisfy a predetermined relation.

9. The output control device according to claim 7, wherein the processing unit is further configured to associate a flag indicating a transition destination state with the state point corresponding to the physiological index value detected by the biosensor at a timing in accordance with detection of a predetermined transition destination manipulation in a case in which the predetermined transition destination manipulation by a user is detected.

10. The output control device according to claim 9, wherein the output control unit is further configured to control output indicating that a current internal state reaches the transition destination state in a case in which the state point associated with the flag indicating the transition destination state and the current state point satisfy a predetermined relation.

11. The output control device according to claim 9, wherein the processing unit is further configured to switch the state point associated with the flag indicating the transition destination state in a case in which the state point associated with the flag indicating the transition source state and the state point associated with the flag indicating the transition destination state are closer than a predetermined distance.

12. The output control device according to claim 1, wherein the physiological index value includes a physiological index value reflecting autonomic nerve activity.

13. The output control device according to claim 12, wherein the physiological index value reflecting the autonomic nerve activity includes a physiological index value based on at least one of a perspiration sensor, an electrocardiographic sensor, a pulse sensor, or a peripheral bloodstream sensor.

14. The output control device according to claim 1, wherein the physiological index value includes a physiological index value reflecting central nerve activity.

15. The output control device according to claim 14, wherein the physiological index value reflecting the central nerve activity includes a physiological index value based on a brain wave sensor.

16. The output control device according to claim 1, wherein a plurality of state points in the physiological index space are classified into a plurality of clusters by machine learning.

17. The output control device according to claim 16, wherein a label added to content output at a timing in accordance with detection of a corresponding physiological index value is associated with each of the plurality of clusters.

18. The output control device according to claim 17, wherein the label is corrected on a basis of evaluation information for the content.

19. An output control method, the method comprising: by a processor,
- receiving a plurality of physiological index values from a biosensor,
- plotting the plurality of physiological index values to a state point in a physiological index space, and
- controlling display of a display object on a graphical computer display in accordance with a change in the state point in the physiological index space corresponding to the physiological index value,
- wherein the controlling of the display of the display object on the graphical computer display is based on a transition speed of the state point in the physiological index space,
- wherein the controlling of the display of the display object on the graphical computer display is in accordance with stability of the state point in the physiological index space,
- wherein the controlling of the display of the display object displayed on the graphical computer display includes controlling an output of the display object displayed on the graphical computer display to be displayed as a graphical animated display object based on the transition speed being greater than a predetermined threshold,
- wherein the graphical animated display object is an animation in which an amplitude or a period of vibration of the display object displayed on the graphical computer display changes according to the stability of the state point in the physiological index space,
- wherein the graphical animated display object is an animation in which a size of the display object changes according to a degree of progress of transition, and
- wherein the degree of progress of transition is calculated in accordance with a position of a current state point in the physiological index space and a positional relation between a transition source cluster and a transition destination cluster.

20. A non-transitory computer-readable medium having embodied thereon a program, which when executed by a computer causes the computer to execute an output control method, the method comprising:
- receiving a plurality of physiological index values from a biosensor,
- plotting the plurality of physiological index values to a state point in a physiological index space, and
- controlling display of a display object on a graphical computer display in accordance with a change in the state point in the physiological index space corresponding to the physiological index value,
- wherein the controlling of the display of the display object on the graphical computer display is based on a transition speed of the state point in the physiological index space,
- wherein the controlling of the display of the display object on the graphical computer display is in accordance with stability of the state point in the physiological index space,
- wherein the controlling of the display of the display object displayed on the graphical computer display includes controlling an output of the display object displayed on the graphical computer display to be displayed as a graphical animated display object based on the transition speed being greater than a predetermined threshold,
- wherein the graphical animated display object is an animation in which an amplitude or a period of vibration of the display object displayed on the graphical computer display changes according to the stability of the state point in the physiological index space,
- wherein the graphical animated display object is an animation in which a size of the display object changes according to a degree of progress of transition, and
- wherein the degree of progress of transition is calculated in accordance with a position of a current state point in the physiological index space and a positional relation between a transition source cluster and a transition destination cluster.

* * * * *